US012721687B2

(12) United States Patent
Crawford et al.

(10) Patent No.: US 12,721,687 B2
(45) **Date of Patent: *Sep. 1, 2026**

(54) SYSTEM FOR NEURONAVIGATION REGISTRATION AND ROBOTIC TRAJECTORY GUIDANCE, AND RELATED METHODS AND DEVICES

(71) Applicant: GLOBUS MEDICAL, INC., Audubon, PA (US)

(72) Inventors: Neil R. Crawford, Chandler, AZ (US); Francisco Ponce, Phoenix, AZ (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/085,451

(22) Filed: Mar. 20, 2025

(65) Prior Publication Data

US 2025/0213159 A1 Jul. 3, 2025

Related U.S. Application Data

(63) Continuation of application No. 18/342,144, filed on Jun. 27, 2023, now Pat. No. 12,268,506, which is a (Continued)

(51) Int. Cl.
*A61B 5/24* (2021.01)
*A61B 5/00* (2006.01)
(Continued)

(52) U.S. Cl.
CPC .............. *A61B 34/30* (2016.02); *A61B 5/055* (2013.01); *A61B 5/6868* (2013.01); *A61B 34/76* (2016.02);
(Continued)

(58) Field of Classification Search
CPC ...... A61B 2034/107; A61B 2034/2055; A61B 2034/2072; A61B 2034/302; A61B 2090/363; A61B 2090/374; A61B 2090/3762; A61B 2090/3954; A61B 2090/3966; A61B 2090/3983; A61B 2505/05; A61B 2560/063; A61B 2562/0209; A61B 2576/00; A61B 34/30; A61B 34/37; A61B 34/76; A61B 5/0035; A61B 5/0077; A61B 5/055; A61B 5/064;
(Continued)

(56) References Cited

U.S. PATENT DOCUMENTS 6,298,262 B1 * 10/2001 Franck .................. A61B 34/20
606/130
11,382,549 B2 * 7/2022 Crawford ............... A61B 5/064
(Continued)

*Primary Examiner* — Michael T Rozanski

(57) ABSTRACT

A position is determined for each fiducial marker of a plurality of fiducial markers in an image volume. Based on the determined positions, a position and orientation of the registration fixture with respect to the anatomical feature is determined. A position is determined for each tracked marker of a first plurality of tracked markers on the registration fixture and a second plurality of tracked markers on the robot arm in a tracking data frame. Based on the determined positions of tracked markers, a position and orientation of the registration fixture and the robot arm of a surgical robot with respect to the tracking space are determined.

20 Claims, 19 Drawing Sheets

Related U.S. Application Data continuation of application No. 17/737,599, filed on May 5, 2022, now Pat. No. 11,737,696, which is a continuation of application No. 16/380,413, filed on Apr. 10, 2019, now Pat. No. 11,382,549, which is a continuation-in-part of application No. 16/361,863, filed on Mar. 22, 2019, now abandoned.

(51) Int. Cl.

| | |
|---|---|
| ***A61B 5/055*** | (2006.01) |
| ***A61B 34/00*** | (2016.01) |
| ***A61B 34/10*** | (2016.01) |
| ***A61B 34/20*** | (2016.01) |
| ***A61B 34/30*** | (2016.01) |
| ***A61B 90/00*** | (2016.01) |
| ***A61B 90/14*** | (2016.01) |

(52) U.S. Cl.

CPC ........ *A61B 90/14* (2016.02); *A61B 2034/107* (2016.02); *A61B 2034/2072* (2016.02); *A61B 2034/302* (2016.02); *A61B 2090/374* (2016.02); *A61B 2090/3762* (2016.02); *A61B 2090/3983* (2016.02); *A61B 2560/063* (2013.01); *A61B 2562/0209* (2013.01)

(58) Field of Classification Search

CPC ... A61B 5/1127; A61B 5/6814; A61B 5/6868; A61B 6/0492; A61B 6/487; A61B 90/14

See application file for complete search history.

(56) References Cited

U.S. PATENT DOCUMENTS

| | | | | |
|---|---|---|---|---|
| 11,737,696 | B2 * | 8/2023 | Crawford | A61B 5/064 600/378 |
| 12,268,506 | B2 * | 4/2025 | Crawford | A61B 5/064 |
| 2017/0265947 | A1 * | 9/2017 | Dyer | A61B 34/20 |

* cited by examiner

400
Exam Image Space 402
Exam Image Space 402
Exam Image Space 402
Exam Image Space 402
Exam Image Space 402
Common Exam Image Space 404
Registration Image Space 408
Verification Image Space 406
Patient Fiducial Coordinates 410
Dynamic Reference Base 412
Dynamic Reference Base 410'
Probe Tracker 416
Robotic Arm Tracker 418
RPS Space 420
Tracking Camera 414

740
742
741
732
750
751
728
730
743
700

SYSTEM FOR NEURONAVIGATION REGISTRATION AND ROBOTIC TRAJECTORY GUIDANCE, AND RELATED METHODS AND DEVICES

CROSS REFERENCE TO RELATED APPLICATIONS

The present application is a continuation of U.S. patent application Ser. No. 18/342,144 filed on Jun. 27, 2023 (published as U.S. Pat. Pub. No. 2024-0008788), which is a continuation of U.S. patent application Ser. No. 17/737,599 filed on May 5, 2022, now 11,737,696, which is a continuation of U.S. patent application Ser. No. 16/380,413 filed on Apr. 10, 2019, now U.S. Pat. No. 11,382,549, which is a continuation-in-part of U.S. patent application Ser. No. 16/361,863 filed on Mar. 22, 2019, (published as U.S. Pat. Pub. No. 2020-0297426), all of which are incorporated in their entireties herein for all purposes.

FIELD

The present disclosure relates to medical devices and systems, and more particularly, systems for neuronavigation registration and robotic trajectory guidance, and related methods and devices.

BACKGROUND

Position recognition systems for robot assisted surgeries are used to determine the position of and track a particular object in 3-dimensions (3D). In robot assisted surgeries, for example, certain objects, such as surgical instruments, need to be tracked with a high degree of precision as the instrument is being positioned and moved by a robot or by a physician, for example.

Position recognition systems may use passive and/or active sensors or markers for registering and tracking the positions of the objects. Using these sensors, the system may geometrically resolve the 3-dimensional position of the sensors based on information from or with respect to one or more cameras, signals, or sensors, etc. These surgical systems can therefore utilize position feedback to precisely guide movement of robotic arms and tools relative to a patients' surgical site. Thus, there is a need for a system that efficiently and accurately provide neuronavigation registration and robotic trajectory guidance in a surgical environment.

SUMMARY

According to some embodiments of inventive concepts, a system includes a processor circuit and a memory coupled to the processor circuit. The memory includes machine-readable instructions configured to cause the processor circuit to determine, based on a first image volume comprising an anatomical feature of a patient, a registration fixture that is fixed with respect to the anatomical feature of the patient, and a first plurality of fiducial markers that are fixed with respect to the registration fixture, determine, for each fiducial marker of the first plurality of fiducial markers, a position of the fiducial marker relative to the image volume. The machine-readable instructions are further configured to cause the processor circuit to determine, based on the determined positions of the first plurality of fiducial markers, a position and orientation of the registration fixture with respect to the anatomical feature. The machine-readable instructions are further configured to cause the processor circuit to, based on a data frame from a tracking system comprising a second plurality of tracking markers that are fixed with respect to the registration fixture, determine, for each tracking marker of the second plurality of tracking markers, a position of the tracking marker. The machine-readable instructions are further configured to cause the processor circuit to determine, based on the determined positions of the second plurality of tracking markers, a position and orientation of the registration fixture with respect to a robot arm of a surgical robot. The machine-readable instructions are further configured to cause the processor circuit to determine, based on the determined position and orientation of the registration fixture with respect to the anatomical feature and the determined position and orientation of the registration fixture with respect to the robot arm, a position and orientation of the anatomical feature with respect to the robot arm. The machine-readable instructions are further configured to cause the processor circuit to control the robot arm based on the determined position and orientation of the anatomical feature with respect to the robot arm.

According to some other embodiments of inventive concepts, a computer-implemented method is disclosed. The computer-implemented method includes, based on a first image volume comprising an anatomical feature of a patient, a registration fixture that is fixed with respect to the anatomical feature of the patient, and a first plurality of fiducial markers that are fixed with respect to the registration fixture, determining, for each fiducial marker of the first plurality of fiducial markers, a position of the fiducial marker. The computer-implemented method further includes determining, based on the determined positions of the first plurality of fiducial markers, a position and orientation of the registration fixture with respect to the anatomical feature. The computer-implemented method further includes, based on a tracking data frame comprising a second plurality of tracking markers that are fixed with respect to the registration fixture, determining, for each tracking marker of the second plurality of tracking markers, a position of the tracking marker. The computer-implemented method further includes determining, based on the determined positions of the second plurality of tracking markers, a position and orientation of the registration fixture with respect to a robot arm of a surgical robot. The computer-implemented method further includes determining, based on the determined position and orientation of the registration fixture with respect to the anatomical feature and the determined position and orientation of the registration fixture with respect to the robot arm, a position and orientation of the anatomical feature with respect to the robot arm. The computer-implemented method further includes controlling the robot arm based on the determined position and orientation of the anatomical feature with respect to the robot arm.

According to some other embodiments of inventive concepts, a surgical system is disclosed. The surgical system includes an intraoperative surgical tracking computer having a processor circuit and a memory. The memory includes machine-readable instructions configured to cause the processor circuit to provide a medical image volume defining an image space. The medical image volume includes an anatomical feature of a patient, a registration fixture that is fixed with respect to the anatomical feature of the patient, and a plurality of fiducial markers that are fixed with respect to the registration fixture. The machine-readable instructions are further configured to cause the processor circuit to, based on the medical image volume, determine, for each fiducial marker of the plurality of fiducial markers, a position of the fiducial marker with respect to the image space. The machine-readable instructions are further configured to cause the processor circuit to determine, based on the determined positions of the plurality of fiducial markers, a position and orientation of the registration fixture with respect to the anatomical feature. The machine-readable instructions are further configured to cause the processor circuit to provide a tracking data frame defining a tracking space, the tracking data frame comprising positions of a first plurality of tracked markers that are fixed with respect to the registration fixture. The machine-readable instructions are further configured to cause the processor circuit to, based on the tracking data frame, determine a position of the anatomical feature with respect to the first plurality of tracked markers in the tracking space. The surgical system further includes a surgical robot having a robot arm configured to position a surgical end-effector. The surgical robot further includes a controller connected to the robot arm. The controller is configured to perform operations including, based on the tracking data frame, determining a position of the robot arm with respect to the tracking space. The controller is configured to perform operations including determining, based on the determined position and orientation of the anatomical feature with respect to the tracking space and the determined position and orientation of the robot arm with respect to the tracking space, a position and orientation of the anatomical feature with respect to the robot arm. The controller is configured to perform operations including controlling movement of the robot arm based on the determined position and orientation of the anatomical feature with respect to the robot arm to position the surgical end-effector relative to a location on the patient to facilitate surgery on the patient.

Other methods and related devices and systems, and corresponding methods and computer program products according to embodiments will be or become apparent to one with skill in the art upon review of the following drawings and detailed description. It is intended that all such devices and systems, and corresponding methods and computer program products be included within this description, be within the scope of the present disclosure, and be protected by the accompanying claims. Moreover, it is intended that all embodiments disclosed herein can be implemented separately or combined in any way and/or combination.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings.

DETAILED DESCRIPTION

Figure 1A:
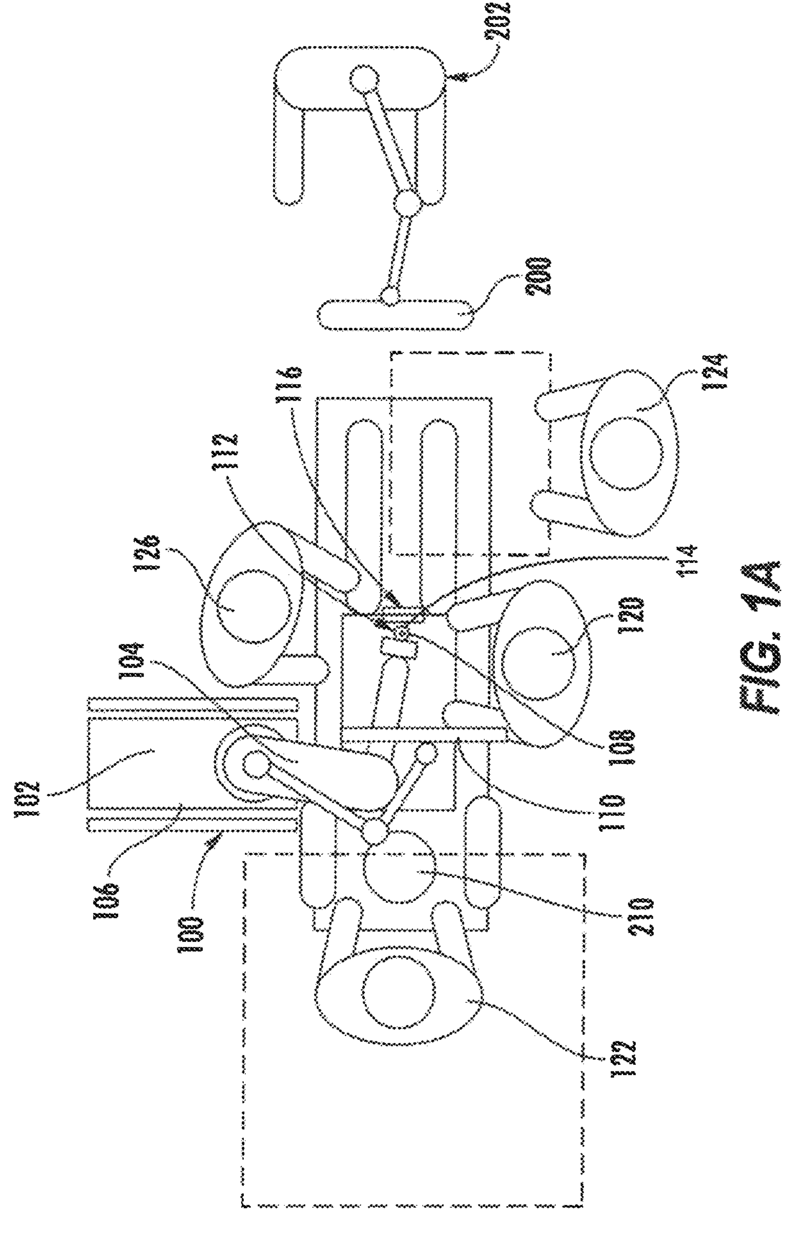
FIG. 1A is an overhead view of an arrangement for locations of a robotic system, patient, surgeon, and other medical personnel during a surgical procedure, according to some embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of “including,” “comprising,” or “having” and variations thereof herein is meant to encompass the items listed thereafter and equivalents thereof as well as additional items. Unless specified or limited otherwise, the terms “mounted,” “connected,” “supported,” and “coupled” and variations thereof are used broadly and encompass both direct and indirect mountings, connections, supports, and couplings. Further, “connected” and “coupled” are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

According to some other embodiments, systems for neuronavigation registration and robotic trajectory guidance, and related methods and devices are disclosed. In some embodiments, a first image having an anatomical feature of a patient, a registration fixture that is fixed with respect to the anatomical feature of the patient, and a first plurality of fiducial markers that are fixed with respect to the registration fixture is analyzed, and a position is determined for each fiducial marker of the first plurality of fiducial markers. Next, based on the determined positions of the first plurality of fiducial markers, a position and orientation of the registration fixture with respect to the anatomical feature is determined. A data frame comprising a second plurality of tracking markers that are fixed with respect to the registration fixture is also analyzed, and a position is determined for each tracking marker of the second plurality of tracking markers. Based on the determined positions of the second plurality of tracking markers, a position and orientation of the registration fixture with respect to a robot arm of a surgical robot is determined. Based on the determined position and orientation of the registration fixture with respect to the anatomical feature and the determined position and orientation of the registration fixture with respect to the robot arm, a position and orientation of the anatomical feature with respect to the robot arm is determined, which allows the robot arm to be controlled based on the determined position and orientation of the anatomical feature with respect to the robot arm.

Advantages of this and other embodiments include the ability to combine neuronavigation and robotic trajectory alignment into one system, with support for a wide variety of different registration hardware and methods. For example, as will be described in detail below, embodiments may support both computerized tomography (CT) and fluoroscopy (fluoro) registration techniques, and may utilize frame-based and/or frameless surgical arrangements. Moreover, in many embodiments, if an initial (e.g. preoperative) registration is compromised due to movement of a registration fixture, registration of the registration fixture (and of the anatomical feature by extension) can be re-established intra-operatively without suspending surgery and re-capturing preoperative images.

Referring now to the drawings, FIG. 1A illustrates a surgical robot system 100 in accordance with an embodiment. Surgical robot system 100 may include, for example, a surgical robot 102, one or more robot arms 104, a base 106, a display 110, an end-effector 112, for example, including a guide tube 114, and one or more tracking markers 118. The robot arm 104 may be movable along and/or about an axis relative to the base 106, responsive to input from a user, commands received from a processing device, or other methods. The surgical robot system 100 may include a patient tracking device 116 also including one or more tracking markers 118, which is adapted to be secured directly to the patient 210 (e.g., to a bone of the patient 210). As will be discussed in greater detail below, the tracking markers 118 may be secured to or may be part of a stereotactic frame that is fixed with respect to an anatomical feature of the patient 210. The stereotactic frame may also be secured to a fixture to prevent movement of the patient 210 during surgery.

Figure 1B:
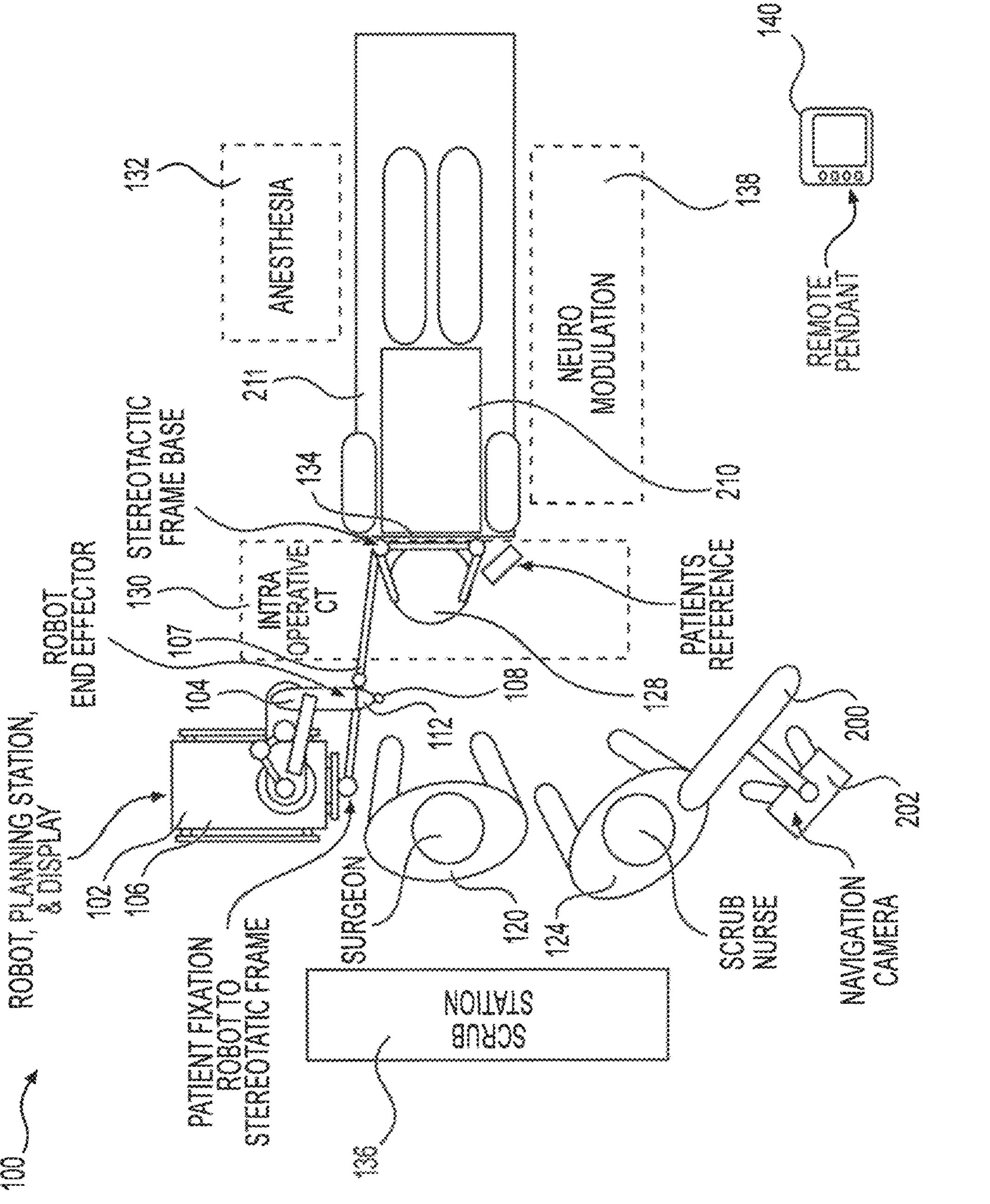
FIG. 1B is an overhead view of an alternate arrangement for locations of a robotic system, patient, surgeon, and other medical personnel during a cranial surgical procedure, according to some embodiments.

According to an alternative embodiment, FIG. 1B is an overhead view of an alternate arrangement for locations of a robotic system 100, patient 210, surgeon 120, and other medical personnel during a cranial surgical procedure. During a cranial procedure, for example, the robot 102 may be positioned behind the head 128 of the patient 210. The robot arm 104 of the robot 102 has an end-effector 112 that may hold a surgical instrument 108 during the procedure. In this example, a stereotactic frame 134 is fixed with respect to the patient's head 128, and the patient 210 and/or stereotactic frame 134 may also be secured to a patient base 211 to prevent movement of the patient's head 128 with respect to the patient base 211. In addition, the patient 210, the stereotactic frame 134 and/or or the patient base 211 may be secured to the robot base 106, such as via an auxiliary arm 107, to prevent relative movement of the patient 210 with respect to components of the robot 102 during surgery. Different devices may be positioned with respect to the patient's head 128 and/or patient base 211 as desired to facilitate the procedure, such as an intra-operative CT device 130, an anesthesiology station 132, a scrub station 136, a neuro-modulation station 138, and/or one or more remote pendants 140 for controlling the robot 102 and/or other devices or systems during the procedure.

Figure 2:
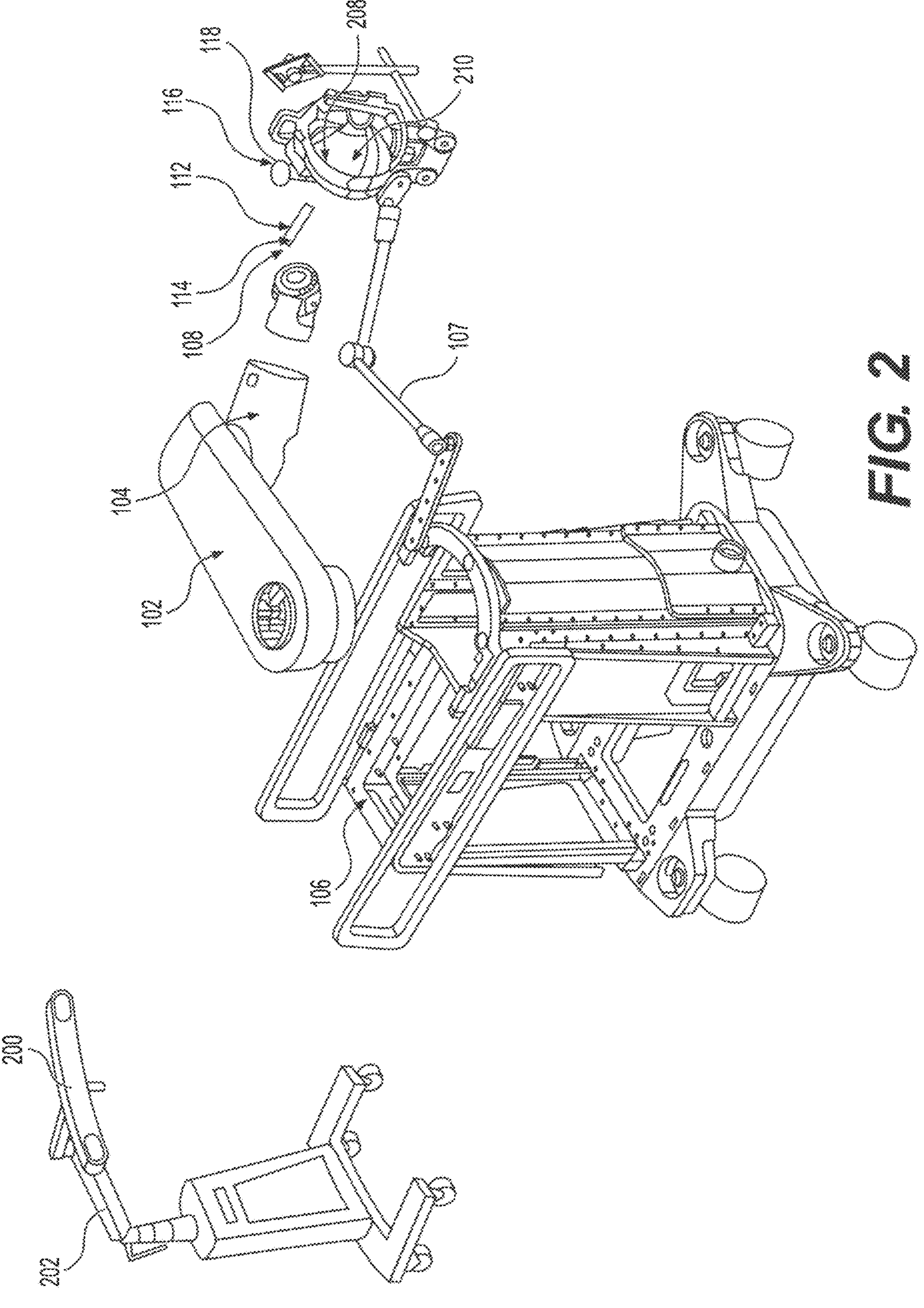
FIG. 2 illustrates a robotic system including positioning of the surgical robot and a camera relative to the patient according to some embodiments.

The surgical robot system 100 in the examples of FIGS. 1A and/or 1B may also use a sensor, such as a camera 200, for example, positioned on a camera stand 202. The camera stand 202 can have any suitable configuration to move, orient, and support the camera 200 in a desired position. The camera 200 may include any suitable camera or cameras, such as one or more cameras (e.g., bifocal or stereophotogrammetric cameras), able to identify, for example, active or passive tracking markers 118 (shown as part of patient tracking device 116 in FIG. 2) in a given measurement volume viewable from the perspective of the camera 200. In this example, the camera 200 may scan the given measurement volume and detect the light that comes from the tracking markers 118 in order to identify and determine the position of the tracking markers 118 in three-dimensions. For example, active tracking markers 118 may include infrared-emitting markers that are activated by an electrical signal (e.g., infrared light emitting diodes (LEDs)), and/or passive tracking markers 118 may include retro-reflective markers that reflect infrared or other light (e.g., they reflect incoming IR radiation into the direction of the incoming light), for example, emitted by illuminators on the camera 200 or other suitable sensor or other device.

In many surgical procedures, one or more targets of surgical interest, such as targets within the brain for example, are localized to an external reference frame. For example, stereotactic neurosurgery may use an externally mounted stereotactic frame that facilitates patient localization and implant insertion via a frame mounted arc. Neuronavigation is used to register, e.g., map, targets within the brain based on pre-operative or intraoperative imaging. Using this pre-operative or intraoperative imaging, links and associations can be made between the imaging and the actual anatomical structures in a surgical environment, and these links and associations can be utilized by robotic trajectory systems during surgery.

According to some embodiments, various software and hardware elements may be combined to create a system that can be used to plan, register, place and verify the location of an instrument or implant in the brain. These systems may integrate a surgical robot, such as the surgical robot 102 of FIGS. 1A and/or 1B, and may employ a surgical navigation system and planning software to program and control the surgical robot. In addition or alternatively, the surgical robot 102 may be remotely controlled, such as by nonsterile personnel.

The robot 102 may be positioned near or next to patient 210, and it will be appreciated that the robot 102 can be positioned at any suitable location near the patient 210 depending on the area of the patient 210 undergoing the operation. The camera 200 may be separated from the surgical robot system 100 and positioned near or next to patient 210 as well, in any suitable position that allows the camera 200 to have a direct visual line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 may remain unimpeded by the locations of the robot 102 and camera 200.

With respect to the other components of the robot 102, the display 110 can be attached to the surgical robot 102 and in other embodiments, the display 110 can be detached from surgical robot 102, either within a surgical room with the surgical robot 102, or in a remote location. The end-effector 112 may be coupled to the robot arm 104 and controlled by at least one motor. In some embodiments, end-effector 112 can comprise a guide tube 114, which is able to receive and orient a surgical instrument 108 used to perform surgery on the patient 210. As used herein, the term "end-effector" is used interchangeably with the terms "end-effectuator" and "effectuator element." Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 108 in a desired manner.

The surgical robot 102 is able to control the translation and orientation of the end-effector 112. The robot 102 is able to move end-effector 112 along x-, y-, and z-axes, for example. The end-effector 112 can be configured for selective rotation about one or more of the x-, y-, and z-axis such that one or more of the Euler Angles (e.g., roll, pitch, and/or yaw) associated with end-effector 112 can be selectively controlled. In some embodiments, selective control of the translation and orientation of end-effector 112 can permit performance of medical procedures with significantly improved accuracy compared to conventional robots that use, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some embodiments, the position of the surgical instrument 108 can be dynamically updated so that surgical robot 102 can be aware of the location of the surgical instrument 108 at all times during the procedure. Consequently, in some embodiments, surgical robot 102 can move the surgical instrument 108 to the desired position quickly without any further assistance from a physician (unless the physician so desires). In some further embodiments, surgical robot 102 can be configured to correct the path of the surgical instrument 108 if the surgical instrument 108 strays from the selected, preplanned trajectory. In some embodiments, surgical robot 102 can be configured to permit stoppage, modification, and/or manual control of the movement of end-effector 112 and/or the surgical instrument 108. Thus, in use, in some embodiments, a physician or other user can operate the system 100, and has the option to stop, modify, or manually control the autonomous movement of end-effector 112 and/or the surgical instrument 108. Further details of surgical robot system 100 including the control and movement of a surgical instrument 108 by surgical robot 102 can be found in co-pending U.S. Patent Publication No. 2013/0345718, which is incorporated herein by reference in its entirety.

As will be described in greater detail below, the surgical robot system 100 can comprise one or more tracking markers configured to track the movement of robot arm 104, end-effector 112, patient 210, and/or the surgical instrument 108 in three dimensions. In some embodiments, a plurality of tracking markers can be mounted (or otherwise secured) thereon to an outer surface of the robot 102, such as, for example and without limitation, on base 106 of robot 102, on robot arm 104, and/or on the end-effector 112. In some embodiments, such as the embodiment of FIG. 3 below, for example, one or more tracking markers can be mounted or otherwise secured to the end-effector 112. One or more tracking markers can further be mounted (or otherwise secured) to the patient 210. In some embodiments, the plurality of tracking markers can be positioned on the patient 210 spaced apart from the surgical field 208 to reduce the likelihood of being obscured by the surgeon, surgical tools, or other parts of the robot 102. Further, one or more tracking markers can be further mounted (or otherwise secured) to the surgical instruments 108 (e.g., a screw driver, dilator, implant inserter, or the like). Thus, the tracking markers enable each of the marked objects (e.g., the end-effector 112, the patient 210, and the surgical instruments 108) to be tracked by the surgical robot system 100. In some embodiments, system 100 can use tracking information collected from each of the marked objects to calculate the orientation and location, for example, of the end-effector 112, the surgical instrument 108 (e.g., positioned in the tube 114 of the end-effector 112), and the relative position of the patient 210. Further details of surgical robot system 100 including the control, movement and tracking of surgical robot 102 and of a surgical instrument 108 can be found in U.S. Patent Publication No. 2016/0242849, which is incorporated herein by reference in its entirety.

In some embodiments, pre-operative imaging may be used to identify the anatomy to be targeted in the procedure. If desired by the surgeon the planning package will allow for the definition of a reformatted coordinate system. This reformatted coordinate system will have coordinate axes anchored to specific anatomical landmarks, such as the anterior commissure (AC) and posterior commissure (PC) for neurosurgery procedures. In some embodiments, multiple pre-operative exam images (e.g., CT or magnetic resonance (MR) images) may be co-registered such that it is possible to transform coordinates of any given point on the anatomy to the corresponding point on all other pre-operative exam images.

As used herein, registration is the process of determining the coordinate transformations from one coordinate system to another. For example, in the co-registration of preoperative images, co-registering a CT scan to an MR scan means that it is possible to transform the coordinates of an anatomical point from the CT scan to the corresponding anatomical location in the MR scan. It may also be advantageous to register at least one exam image coordinate system to the coordinate system of a common registration fixture, such as a dynamic reference base (DRB), which may allow the camera 200 to keep track of the position of the patient in the camera space in real-time so that any intraoperative movement of an anatomical point on the patient in the room can be detected by the robot system 100 and accounted for by compensatory movement of the surgical robot 102.

Figure 3:
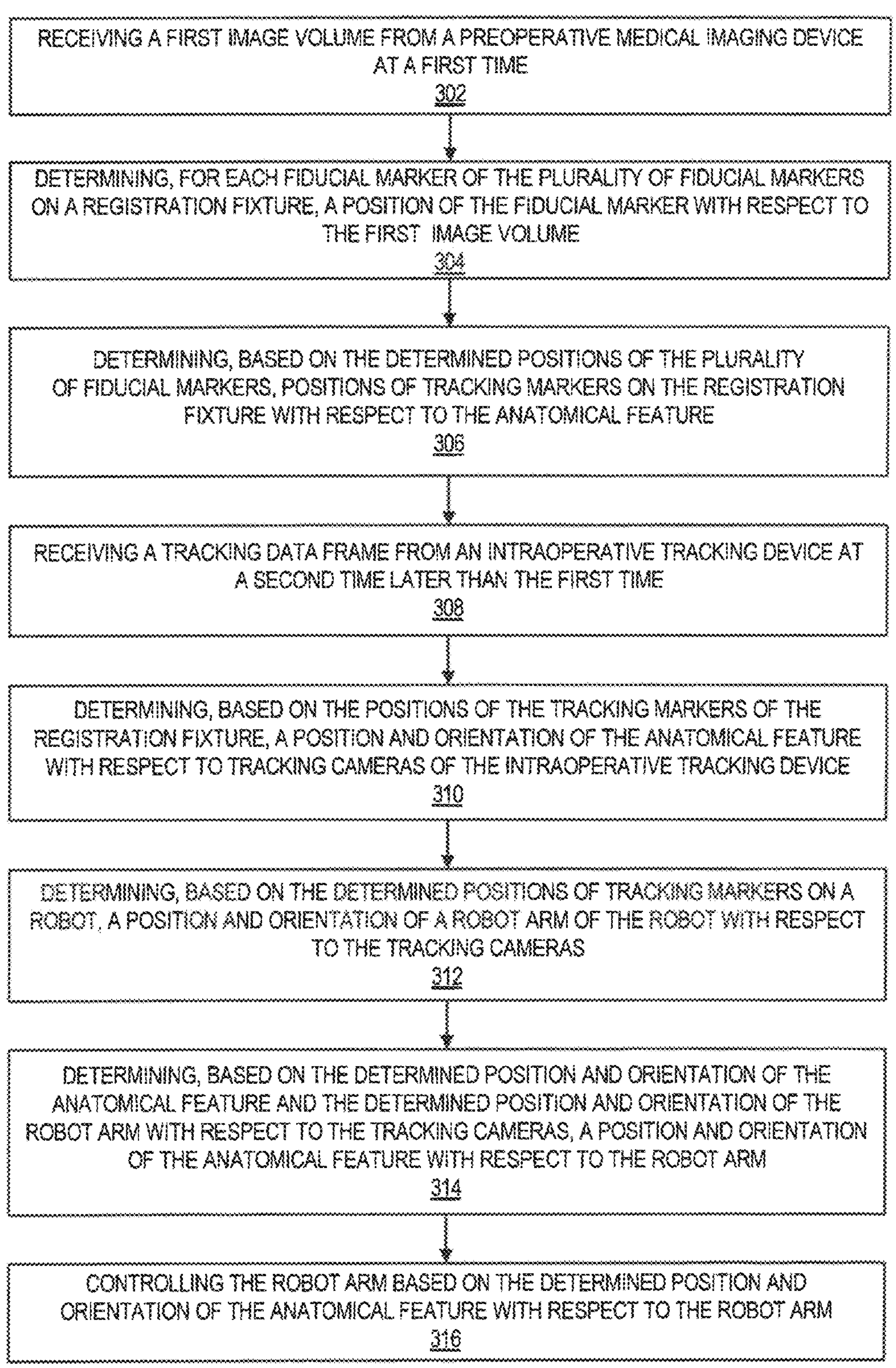
FIG. 3 is a flowchart diagram illustrating computer-implemented operations for determining a position and orientation of an anatomical feature of a patient with respect to a robot arm of a surgical robot, according to some embodiments.

FIG. 3 is a flowchart diagram illustrating computer-implemented operations 300 for determining a position and orientation of an anatomical feature of a patient with respect to a robot arm of a surgical robot, according to some embodiments. The operations 300 may include receiving a first image volume, such as a CT scan, from a preoperative image capture device at a first time (Block 302). The first image volume includes an anatomical feature of a patient and at least a portion of a registration fixture that is fixed with respect to the anatomical feature of the patient. The registration fixture includes a first plurality of fiducial markers that are fixed with respect to the registration fixture. The operations 300 further include determining, for each fiducial marker of the first plurality of fiducial markers, a position of the fiducial marker relative to the first image volume (Block 304). The operations 300 further include, determining, based on the determined positions of the first plurality of fiducial markers, positions of an array of tracking markers on the registration fixture (fiducial registration array or FRA) with respect to the anatomical feature (Block 306).

The operations 300 may further include receiving a tracking data frame from an intraoperative tracking device comprising a plurality of tracking cameras at a second time that is later than the first time (Block 308). The tracking frame includes positions of a plurality of tracking markers that are fixed with respect to the registration fixture (FRA) and a plurality of tracking markers that are fixed with respect to the robot. The operations 300 further include determining, for based on the positions of tracking markers of the registration fixture, a position and orientation of the anatomical feature with respect to the tracking cameras (Block 310). The operations 300 further include determining, based on the determined positions of the plurality of tracking markers on the robot, a position and orientation of the robot arm of a surgical robot with respect to the tracking cameras (Block 312).

The operations 300 further include determining, based on the determined position and orientation of the anatomical feature with respect to the tracking cameras and the determined position and orientation of the robot arm with respect to the tracking cameras, a position and orientation of the anatomical feature with respect to the robot arm (Block 314). The operations 300 further include controlling movement of the robot arm with respect to the anatomical feature, e.g., along and/or rotationally about one or more defined axis, based on the determined position and orientation of the anatomical feature with respect to the robot arm (Block 316).

Figure 4:
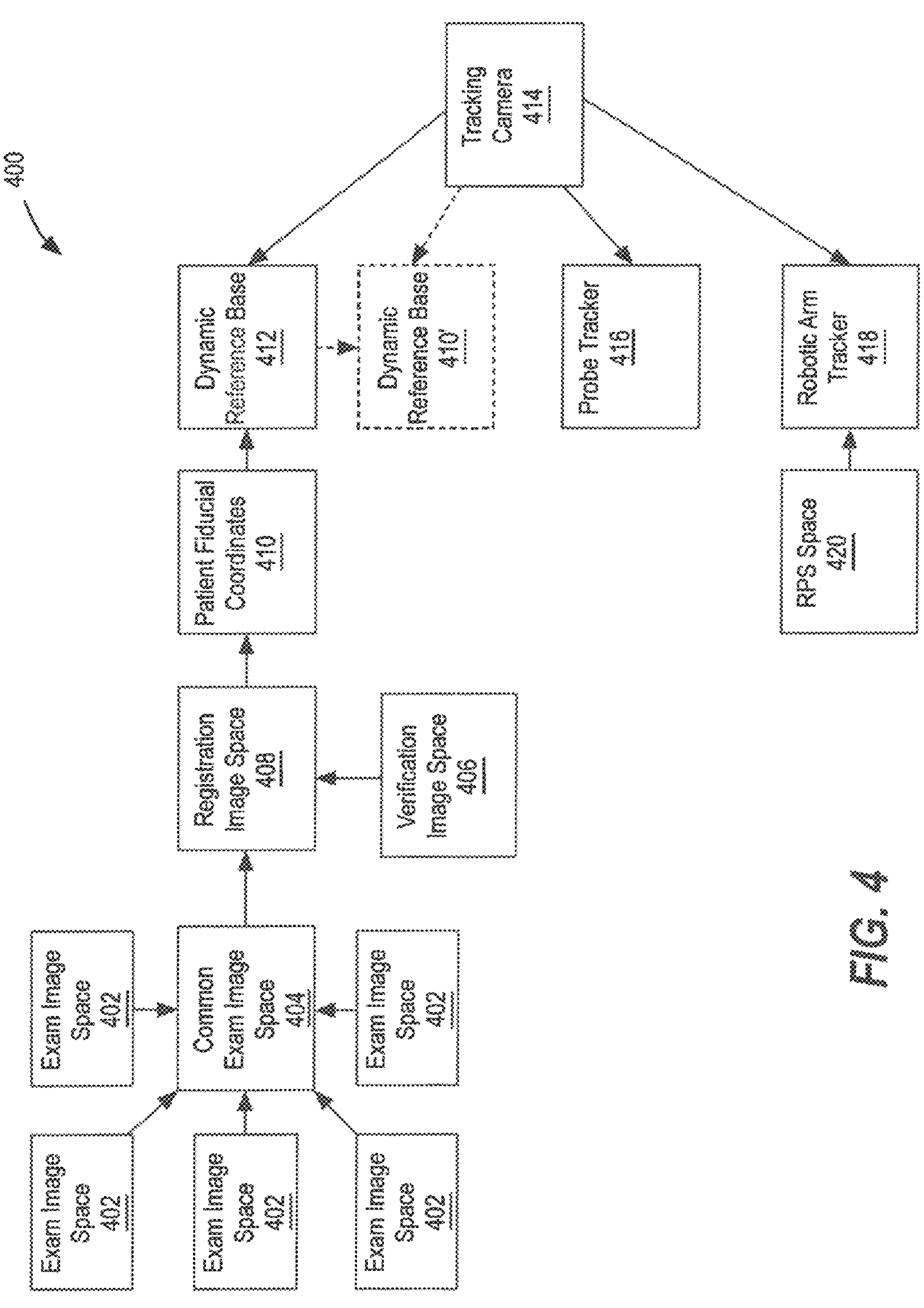
FIG. 4 is a diagram illustrating processing of data for determining a position and orientation of an anatomical feature of a patient with respect to a robot arm of a surgical robot, according to some embodiments.

FIG. 4 is a diagram illustrating a data flow 400 for a multiple coordinate transformation system, to enable determining a position and orientation of an anatomical feature of a patient with respect to a robot arm of a surgical robot, according to some embodiments. In this example, data from a plurality of exam image spaces 402, based on a plurality of exam images, may be transformed and combined into a common exam image space 404. The data from the common exam image space 404 and data from a verification image space 406, based on a verification image, may be transformed and combined into a registration image space 408. Data from the registration image space 408 may be transformed into patient fiducial coordinates 410, which is transformed into coordinates for a DRB 412. A tracking camera 414 may detect movement of the DRB 412 (represented by DRB 412') and may also detect a location of a probe tracker 416 to track coordinates of the DRB 412 over time. A robotic arm tracker 418 determines coordinates for the robot arm based on transformation data from a Robotics Planning System (RPS) space 420 or similar modeling system, and/or transformation data from the tracking camera 414.

It should be understood that these and other features may be used and combined in different ways to achieve registration of image space, i.e., coordinates from image volume, into tracking space, i.e., coordinates for use by the surgical robot in real-time. As will be discussed in detail below, these features may include fiducial-based registration such as stereotactic frames with CT localizer, preoperative CT or MRI registered using intraoperative fluoroscopy, calibrated scanner registration where any acquired scan's coordinates are pre-calibrated relative to the tracking space, and/or surface registration using a tracked probe, for example.

Figure 5A:
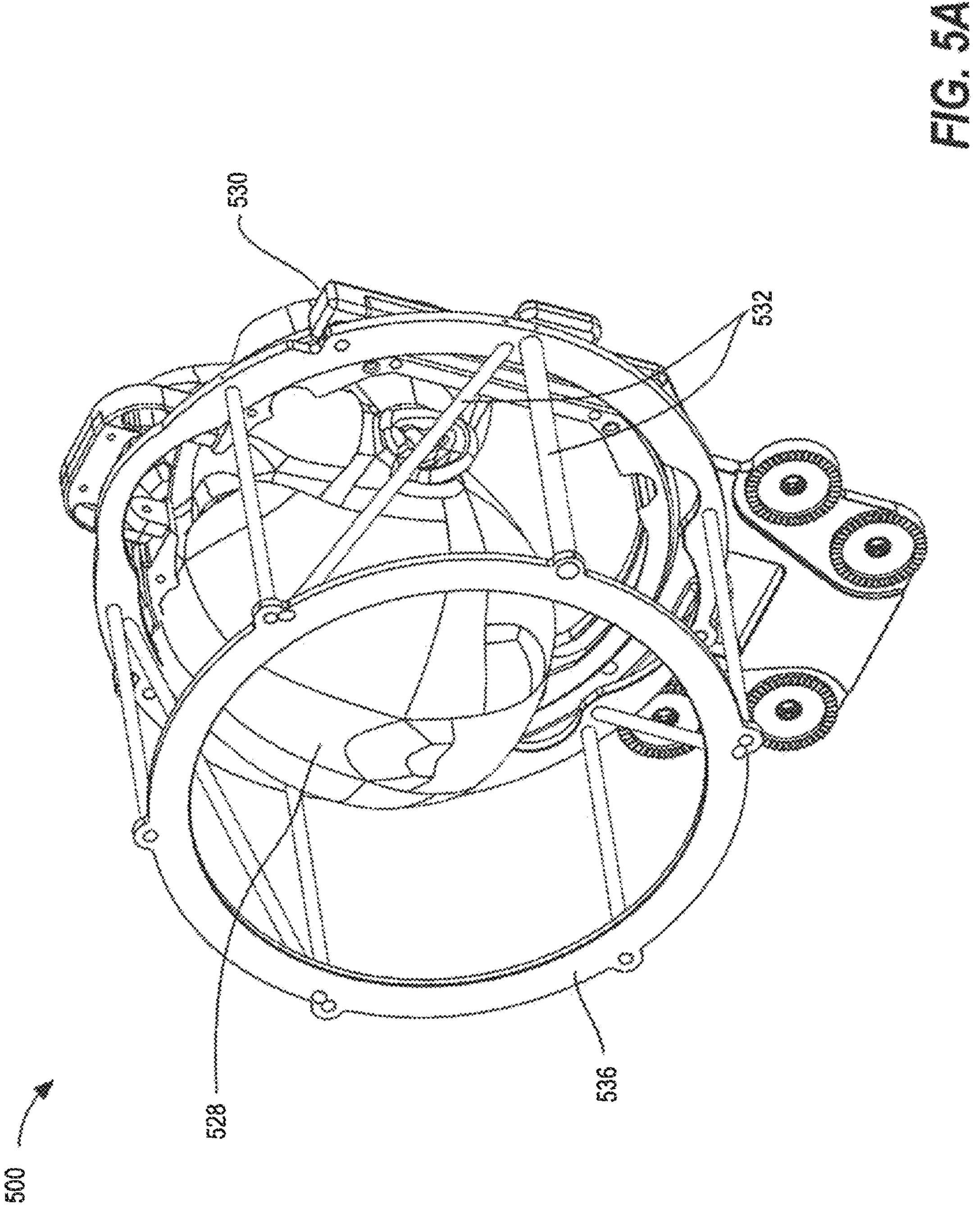
FIGS. 5A-5C illustrate a system for registering an anatomical feature of a patient using a computerized tomography (CT) localizer, a frame reference array (FRA), and a dynamic reference base (DRB), according to some embodiments.
Figure 5B:
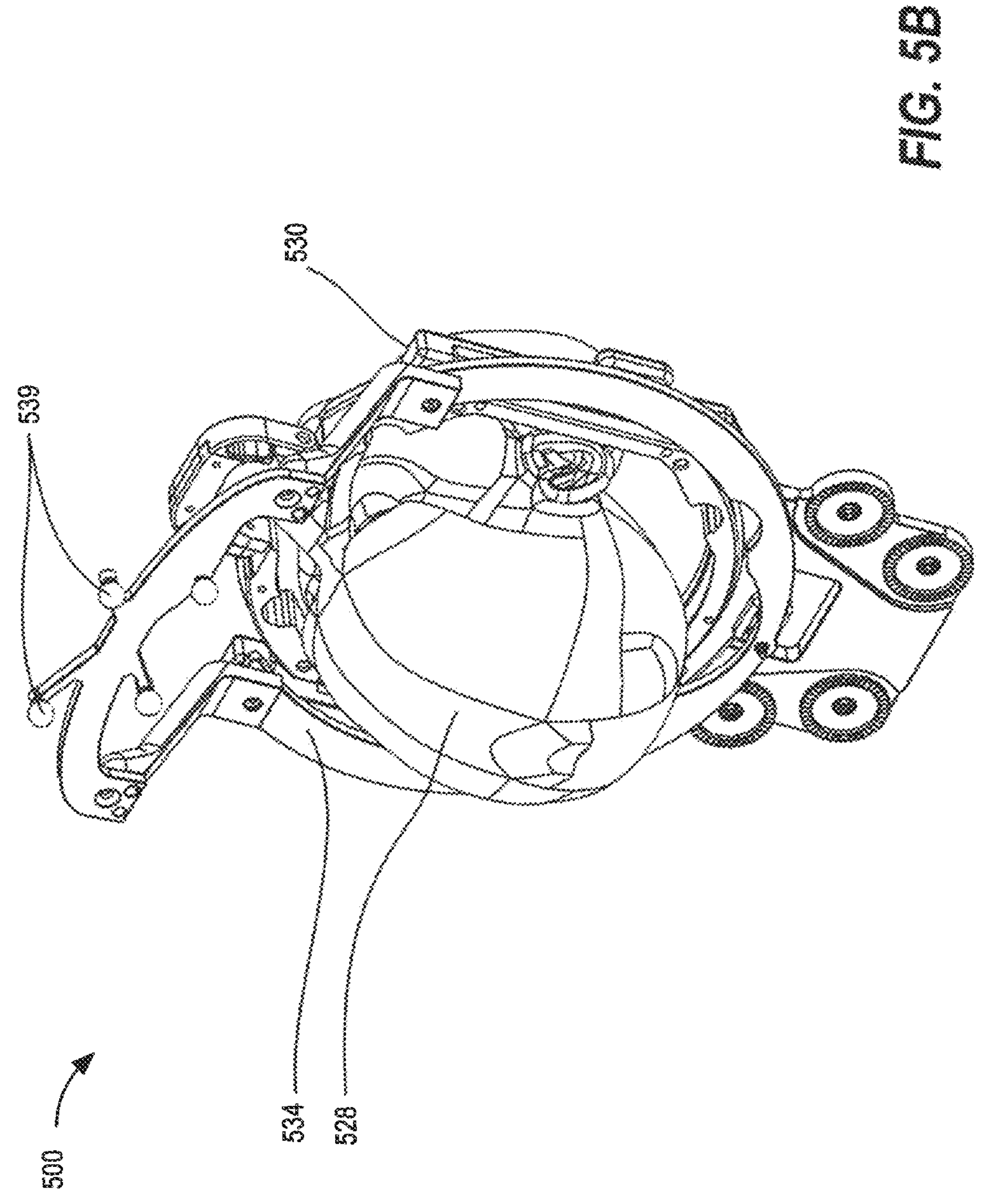
Figure 5C:
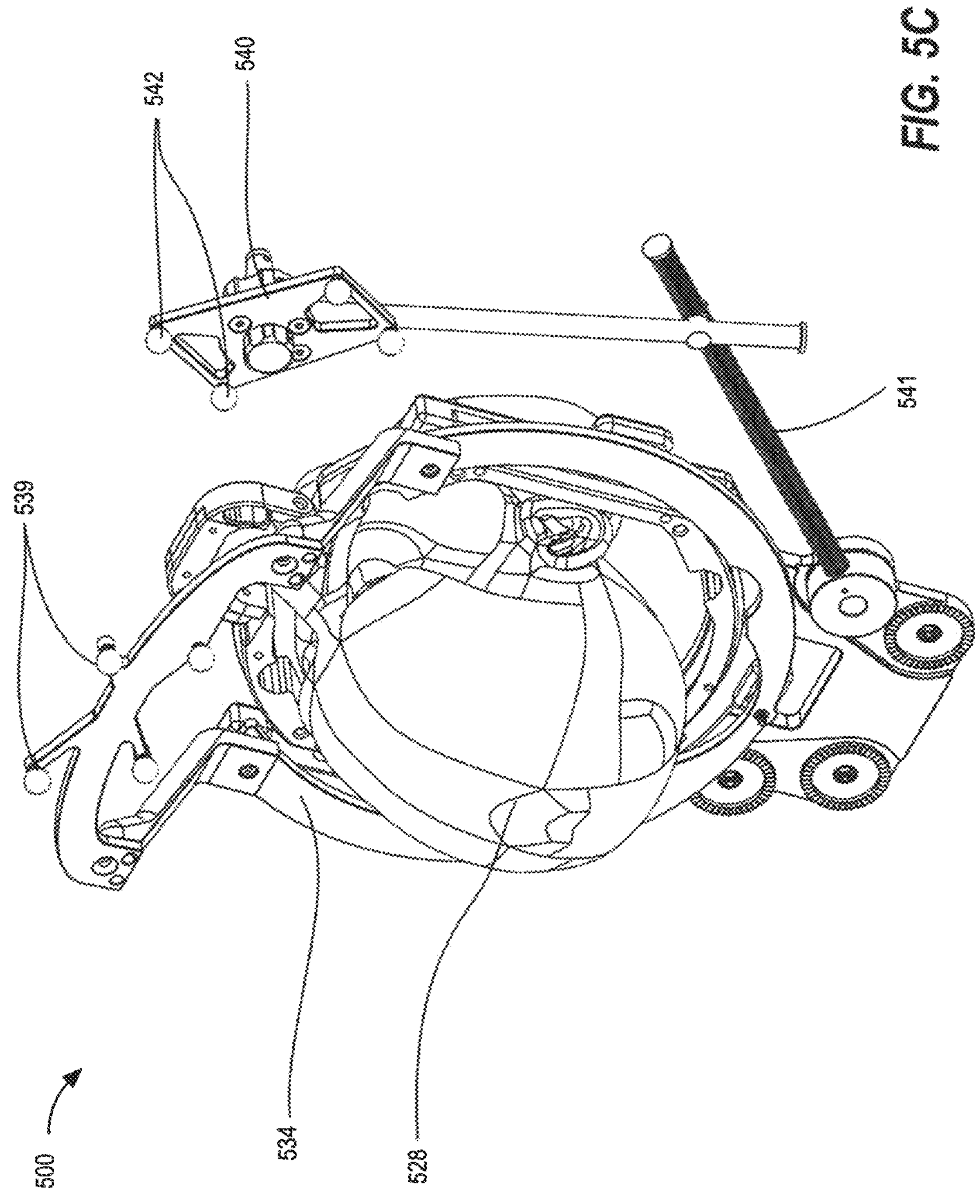

In one example, FIGS. 5A-5C illustrate a system 500 for registering an anatomical feature of a patient. In this example, the stereotactic frame base 530 is fixed to an anatomical feature 528 of patient, e.g., the patient's head. As shown by FIG. 5A, the stereotactic frame base 530 may be affixed to the patient's head 528 prior to registration using pins clamping the skull or other method. The stereotactic frame base 530 may act as both a fixation platform, for holding the patient's head 528 in a fixed position, and registration and tracking platform, for alternatingly holding the CT localizer 536 or the FRA fixture 534. The CT localizer 536 includes a plurality of fiducial markers 532 (e.g., N-pattern radio-opaque rods or other fiducials), which are automatically detected in the image space using image processing. Due to the precise attachment mechanism of the CT localizer 536 to the base 530, these fiducial markers 532 are in known space relative to the stereotactic frame base 530. A 3D CT scan of the patient with CT localizer 536 attached is taken, with an image volume that includes both the patient's head 528 and the fiducial markers 532 of the CT localizer 536. This registration image can be taken intraoperatively or preoperatively, either in the operating room or in radiology, for example. The captured 3D image dataset is stored to computer memory.

As shown by FIG. 5B, after the registration image is captured, the CT localizer 536 is removed from the stereotactic frame base 530 and the frame reference array fixture 534 is attached to the stereotactic frame base 530. The stereotactic frame base 530 remains fixed to the patient's head 528, however, and is used to secure the patient during surgery, and serves as the attachment point of a frame reference array fixture 534. The frame reference array fixture 534 includes a frame reference array (FRA), which is a rigid array of three or more tracked markers 539, which may be the primary reference for optical tracking. By positioning the tracked markers 539 of the FRA in a fixed, known location and orientation relative to the stereotactic frame base 530, the position and orientation of the patient's head 528 may be tracked in real time. Mount points on the FRA fixture 534 and stereotactic frame base 530 may be designed such that the FRA fixture 534 attaches reproducibly to the stereotactic frame base 530 with minimal (i.e., submillimetric) variability. These mount points on the stereotactic frame base 530 can be the same mount points used by the CT localizer 536, which is removed after the scan has been taken. An auxiliary arm (such as auxiliary arm 107 of FIG. 1B, for example) or other attachment mechanism can also be used to securely affix the patient to the robot base to ensure that the robot base is not allowed to move relative to the patient.

As shown by FIG. 5C, a dynamic reference base (DRB) 540 may also be attached to the stereotactic frame base 530. The DRB 540 in this example includes a rigid array of three or more tracked markers 542. In this example, the DRB 540 and/or other tracked markers may be attached to the stereotactic frame base 530 and/or to directly to the patient's head 528 using auxiliary mounting arms 541, pins, or other attachment mechanisms. Unlike the FRA fixture 534, which mounts in only one way for unambiguous localization of the stereotactic frame base 530, the DRB 540 in general may be attached as needed for allowing unhindered surgical and equipment access. Once the DRB 540 and FRA fixture 534 are attached, registration, which was initially related to the tracking markers 539 of the FRA, can be optionally transferred or related to the tracking markers 542 of the DRB 540. For example, if any part of the FRA fixture 534 blocks surgical access, the surgeon may remove the FRA fixture 534 and navigate using only the DRB 540. However, if the FRA fixture 534 is not in the way of the surgery, the surgeon could opt to navigate from the FRA markers 539, without using a DRB 540, or may navigate using both the FRA markers 539 and the DRB 540. In this example, the FRA fixture 534 and/or DRB 540 uses optical markers, the tracked positions of which are in known locations relative to the stereotactic frame base 530, similar to the CT localizer 536, but it should be understood that many other additional and/or alternative techniques may be used.

Figure 6A:
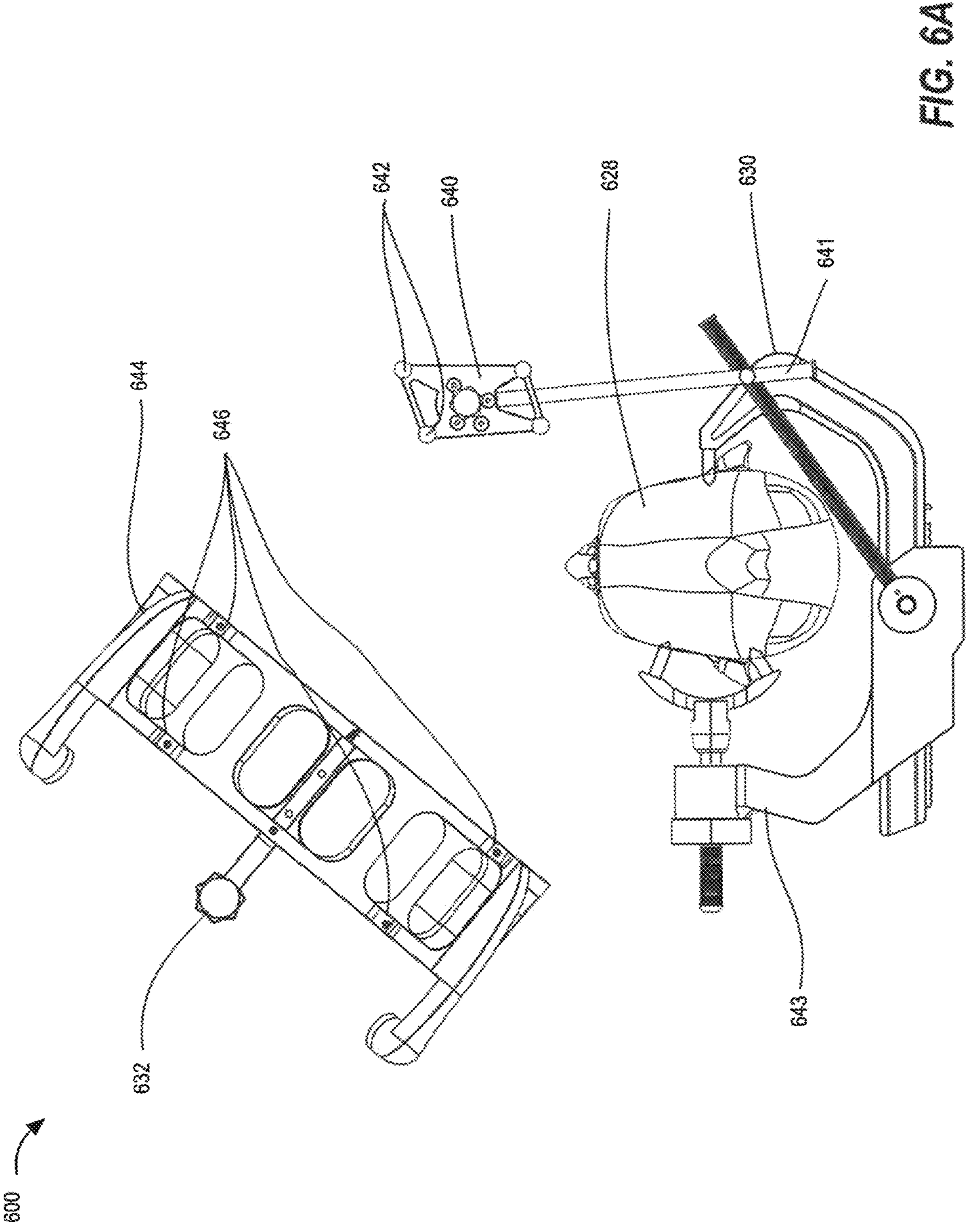
FIGS. 6A and 6B illustrate a system for registering an anatomical feature of a patient using fluoroscopy (fluoro) imaging, according to some embodiments.
Figure 6B:
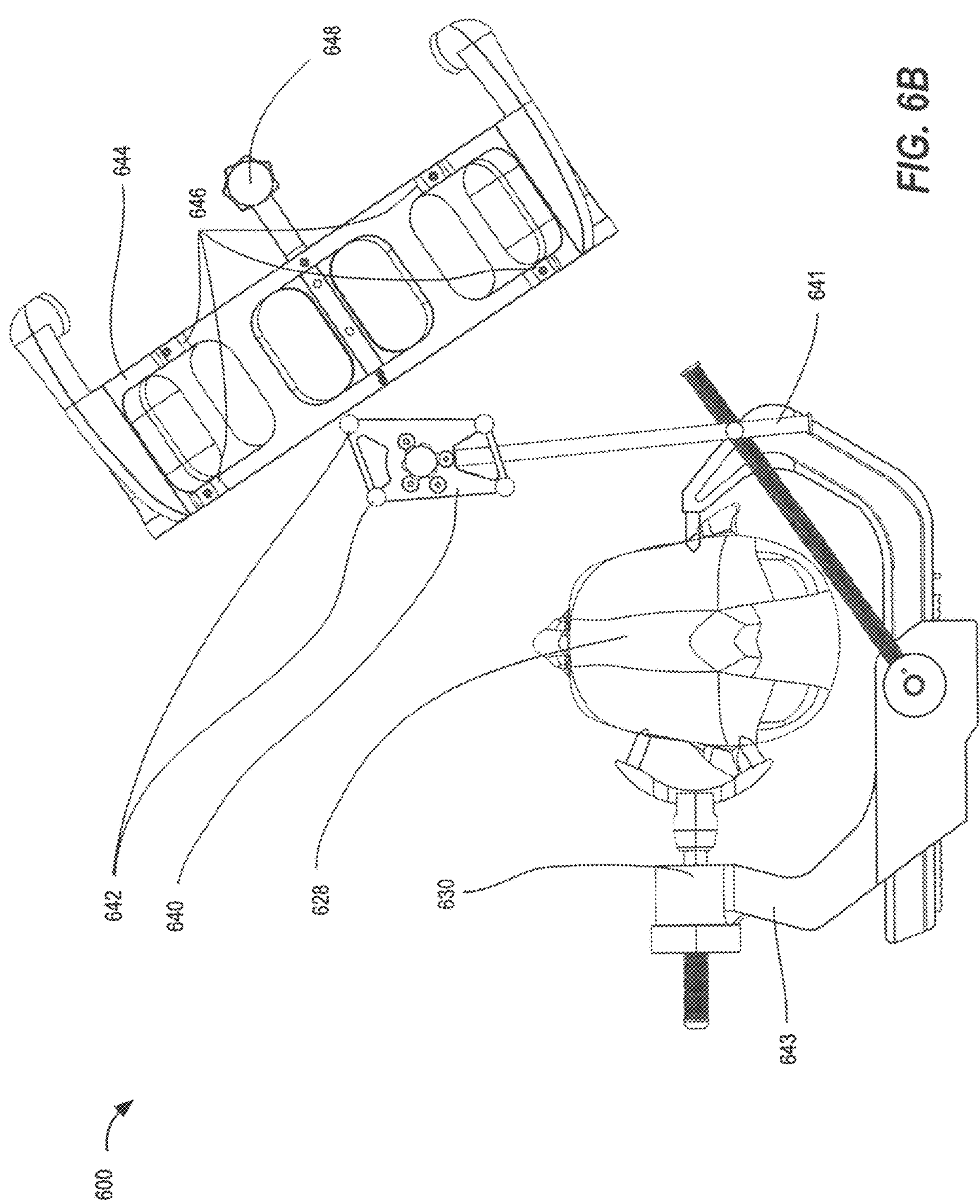

FIGS. 6A and 6B illustrate a system 600 for registering an anatomical feature of a patient using fluoroscopy (fluoro) imaging, according to some embodiments. In this embodiment, image space is registered to tracking space using multiple intraoperative fluoroscopy (fluoro) images taken using a tracked registration fixture 644. The anatomical feature of the patient (e.g., the patient's head 628) is positioned and rigidly affixed in a clamping apparatus 643 in a static position for the remainder of the procedure. The clamping apparatus 643 for rigid patient fixation can be a three-pin fixation system such as a Mayfield clamp, a stereotactic frame base attached to the surgical table, or another fixation method, as desired. The clamping apparatus 643 may also function as a support structure for a patient tracking array or DRB 640 as well. The DRB may be attached to the clamping apparatus using auxiliary mounting arms 641 or other means.

Once the patient is positioned, the fluoro fixture 644 is attached the fluoro unit's x-ray collecting image intensifier (not shown) and secured by tightening clamping feet 632. The fluoro fixture 644 contains fiducial markers (e.g., metal spheres laid out across two planes in this example, not shown) that are visible on 2D fluoro images captured by the fluoro image capture device and can be used to calculate the location of the x-ray source relative to the image intensifier, which is typically about 1 meter away contralateral to the patient, using a standard pinhole camera model. Detection of the metal spheres in the fluoro image captured by the fluoro image capture device also enables the software to de-warp the fluoro image (i.e., to remove pincushion and s-distortion). Additionally, the fluoro fixture 644 contains 3 or more tracking markers 646 for determining the location and orientation of the fluoro fixture 644 in tracking space. In some embodiments, software can project vectors through a CT image volume, based on a previously captured CT image, to generate synthetic images based on contrast levels in the CT image that appear similar to the actual fluoro images (i.e., digitally reconstructed radiographs (DRRs)). By iterating through theoretical positions of the fluoro beam until the DRRs match the actual fluoro shots, a match can be found between fluoro image and DRR in two or more perspectives, and based on this match, the location of the patient's head 628 relative to the x-ray source and detector is calculated. Because the tracking markers 646 on the fluoro fixture 644 track the position of the image intensifier and the position of the x-ray source relative to the image intensifier is calculated from metal fiducials on the fluoro fixture 644 projected on 2D images, the position of the x-ray source and detector in tracking space are known and the system is able to achieve image-to-tracking registration.

As shown by FIGS. 6A and 6B, two or more shots are taken of the head 628 of the patient by the fluoro image capture device from two different perspectives while tracking the array markers 642 of the DRB 640, which is fixed to the registration fixture 630 via a mounting arm 641, and tracking markers 646 on the fluoro fixture 644. Based on the tracking data and fluoro data, an algorithm computes the location of the head 628 or other anatomical feature relative to the tracking space for the procedure. Through image-to-tracking registration, the location of any tracked tool in the image volume space can be calculated.

For example, in one embodiment, a first fluoro image taken from a first fluoro perspective can be compared to a first DRR constructed from a first perspective through a CT image volume, and a second fluoro image taken from a second fluoro perspective can be compared to a second DRR constructed from a second perspective through the same CT image volume. Based on the comparisons, it may be determined that the first DRR is substantially equivalent to the first fluoro image with respect to the projected view of the anatomical feature, and that the second DRR is substantially equivalent to the second fluoro image with respect to the projected view of the anatomical feature. Equivalency confirms that the position and orientation of the x-ray path from emitter to collector on the actual fluoro machine as tracked in camera space matches the position and orientation of the x-ray path from emitter to collector as specified when generating the DRRs in CT space, and therefore registration of tracking space to CT space is achieved.

Figure 7:
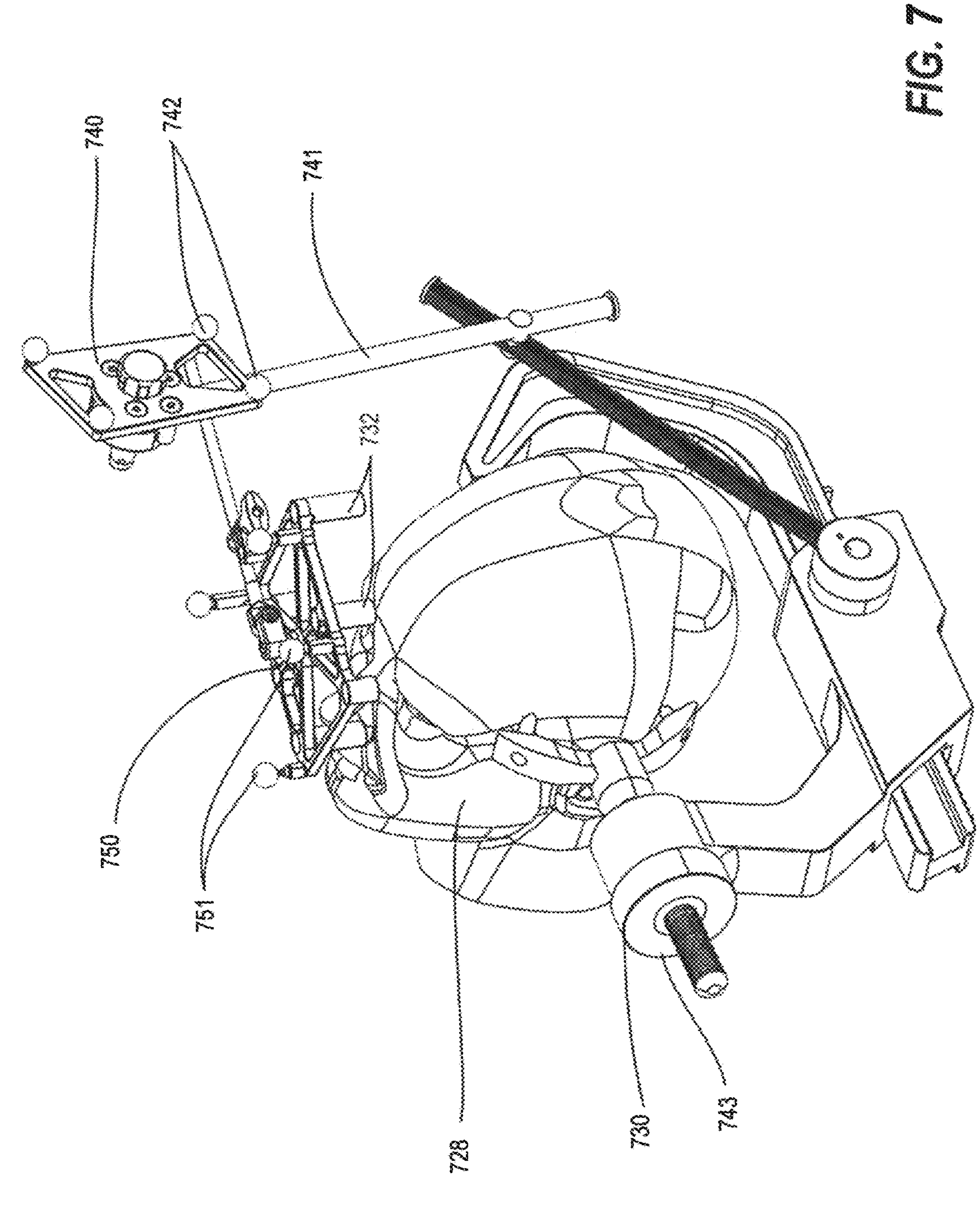
FIG. 7 illustrates a system for registering an anatomical feature of a patient using an intraoperative CT fixture (ICT) and a DRB, according to some embodiments.

FIG. 7 illustrates a system 700 for registering an anatomical feature of a patient using an intraoperative CT fixture (ICT) and a DRB, according to some embodiments. As shown in FIG. 7, in one application, a fiducial-based image-to-tracking registration can be utilized that uses an intraoperative CT fixture (ICT) 750 having a plurality of tracking markers 751 and radio-opaque fiducial reference markers 732 to register the CT space to the tracking space. After stabilizing the anatomical feature 728 (e.g., the patient's head) using clamping apparatus 730 such as a three-pin Mayfield frame and/or stereotactic frame, the surgeon will affix the ICT 750 to the anatomical feature 728, DRB 740, or clamping apparatus 730, so that it is in a static position relative to the tracking markers 742 of the DRB 740, which may be held in place by mounting arm 741 or other rigid means. A CT scan is captured that encompasses the fiducial reference markers 732 of the ICT 750 while also capturing relevant anatomy of the anatomical feature 728. Once the CT scan is loaded in the software, the system auto-identifies (through image processing) locations of the fiducial reference markers 732 of the ICT within the CT volume, which are in a fixed position relative to the tracking markers of the ICT 750, providing image-to-tracking registration. This registration, which was initially based on the tracking markers 751 of the ICT 750, is then related to or transferred to the tracking markers 742 of the DRB 740, and the ICT 750 may then be removed.

Figure 8A:
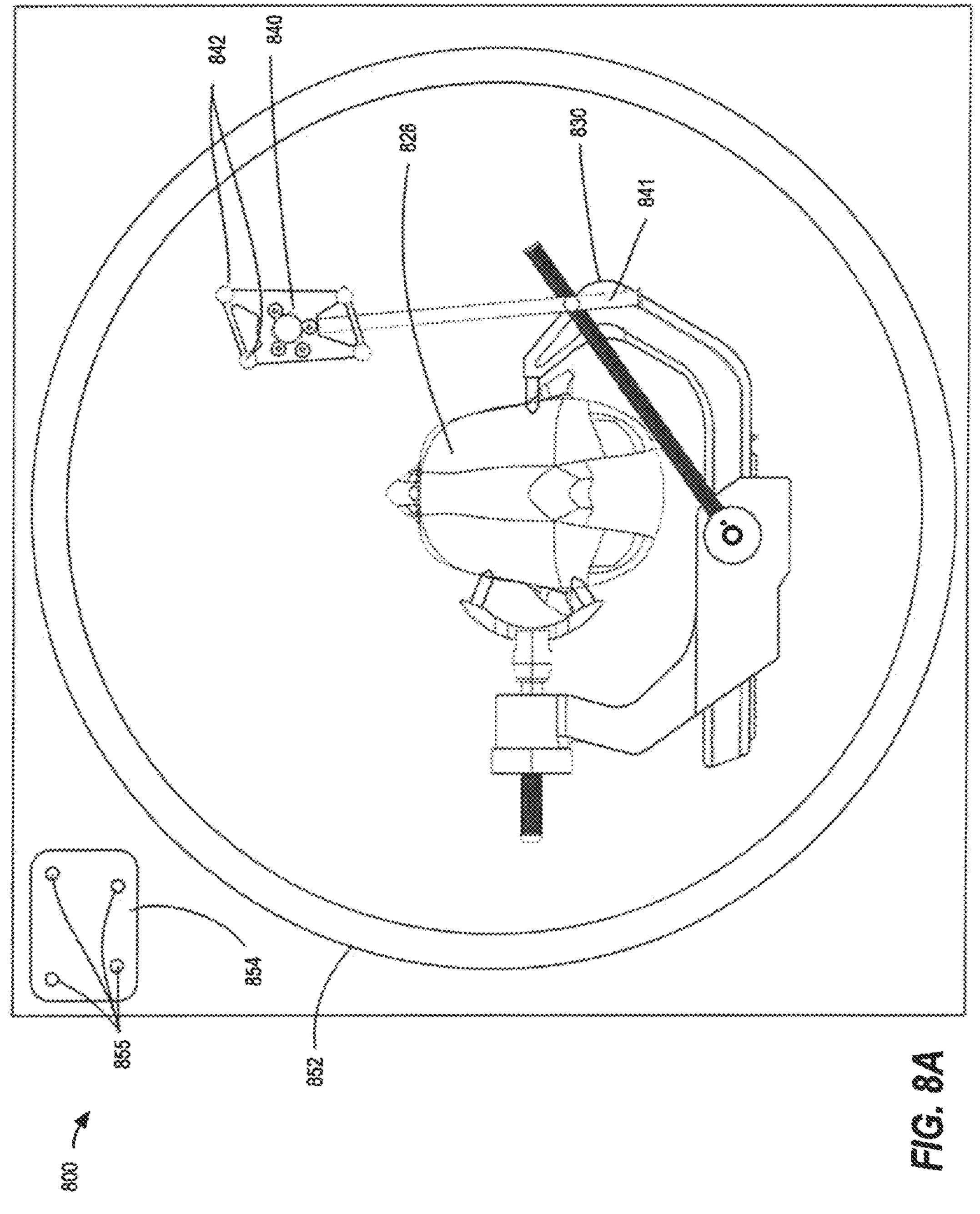
FIGS. 8A and 8B illustrate systems for registering an anatomical feature of a patient using a DRB and an X-ray cone beam imaging device, according to some embodiments.

FIG. 8A illustrates a system 800 for registering an anatomical feature of a patient using a DRB and an X-ray cone beam imaging device, according to some embodiments. An intraoperative scanner 852, such as an X-ray machine or other scanning device, may have a tracking array 854 with tracking markers 855, mounted thereon for registration. Based on the fixed, known position of the tracking array 854 on the scanning device, the system may be calibrated to directly map (register) the tracking space to the image space of any scan acquired by the system. Once registration is achieved, the registration, which is initially based on the tracking markers 855 (e.g. gantry markers) of the scanner's array 854, is related or transferred to the tracking markers 842 of a DRB 840, which may be fixed to a clamping fixture 830 holding the patient's head 828 by a mounting arm 841 or other rigid means. After transferring registration, the markers on the scanner are no longer used and can be removed, deactivated or covered if desired. Registering the tracking space to any image acquired by a scanner in this way may avoid the need for fiducials or other reference markers in the image space in some embodiments.

Figure 8B:
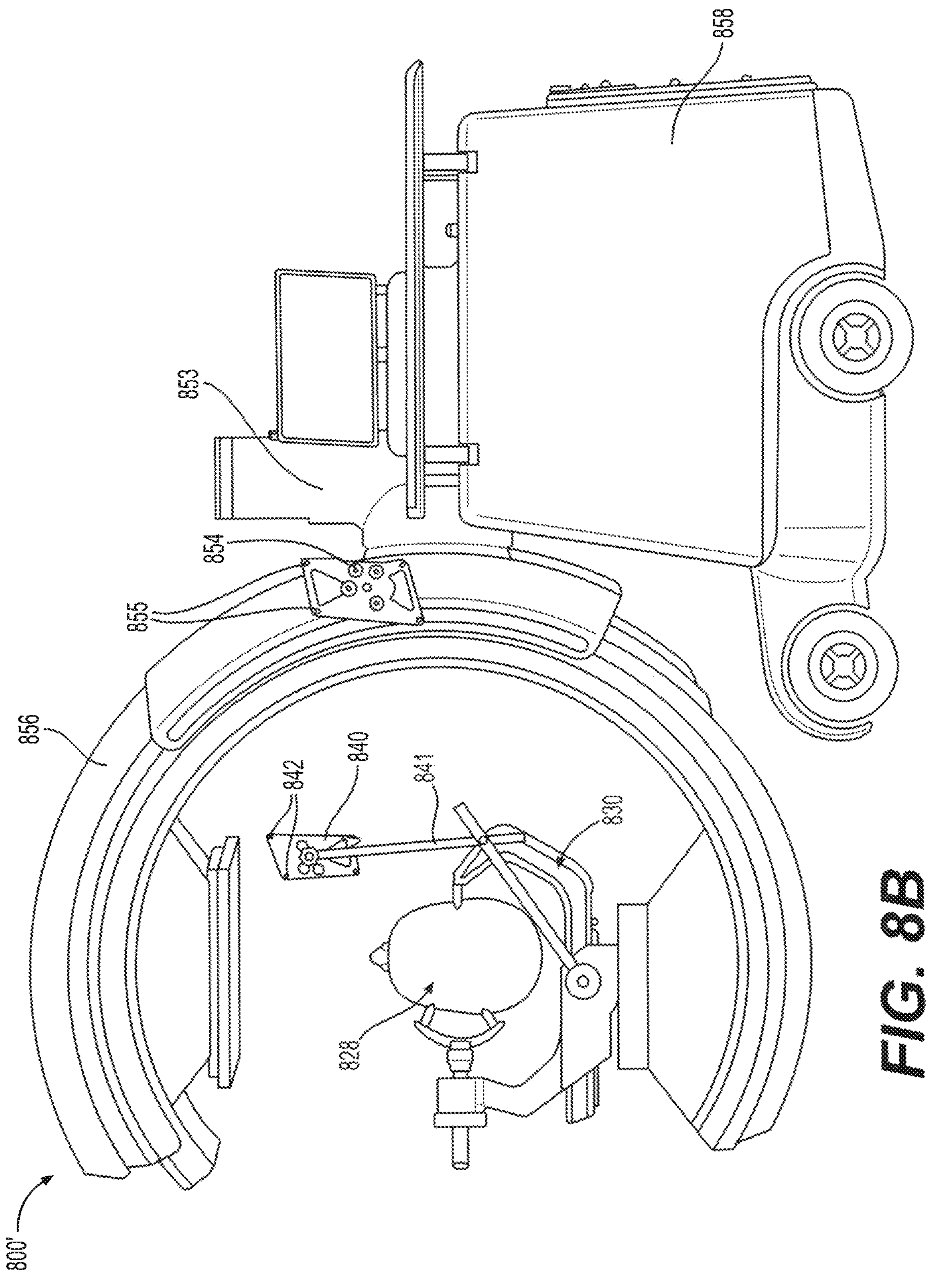

FIG. 8B illustrates an alternative system 800' that uses a portable intraoperative scanner, referred to herein as a C-arm scanner 853. In this example, the C-arm scanner 853 includes a c-shaped arm 856 coupled to a movable base 858 to allow the C-arm scanner 853 to be moved into place and removed as needed, without interfering with other aspects of the surgery. The arm 856 is positioned around the patient's head 828 intraoperatively, and the arm 856 is rotated and/or translated with respect to the patient's head 828 to capture the X-ray or other type of scan that to achieve registration, at which point the C-arm scanner 853 may be removed from the patient.

Another registration method for an anatomical feature of a patient, e.g., a patient's head, may be to use a surface contour map of the anatomical feature, according to some embodiments. A surface contour map may be constructed using a navigated or tracked probe, or other measuring or sensing device, such as a laser pointer, 3D camera, etc. For example, a surgeon may drag or sequentially touch points on the surface of the head with the navigated probe to capture the surface across unique protrusions, such as zygomatic bones, superciliary arches, bridge of nose, eyebrows, etc. The system then compares the resulting surface contours to contours detected from the CT and/or MR images, seeking the location and orientation of contour that provides the closest match. To account for movement of the patient and to ensure that all contour points are taken relative to the same anatomical feature, each contour point is related to tracking markers on a DRB on the patient at the time it is recorded. Since the location of the contour map is known in tracking space from the tracked probe and tracked DRB, tracking-to-image registration is obtained once the corresponding contour is found in image space.

Figure 9:
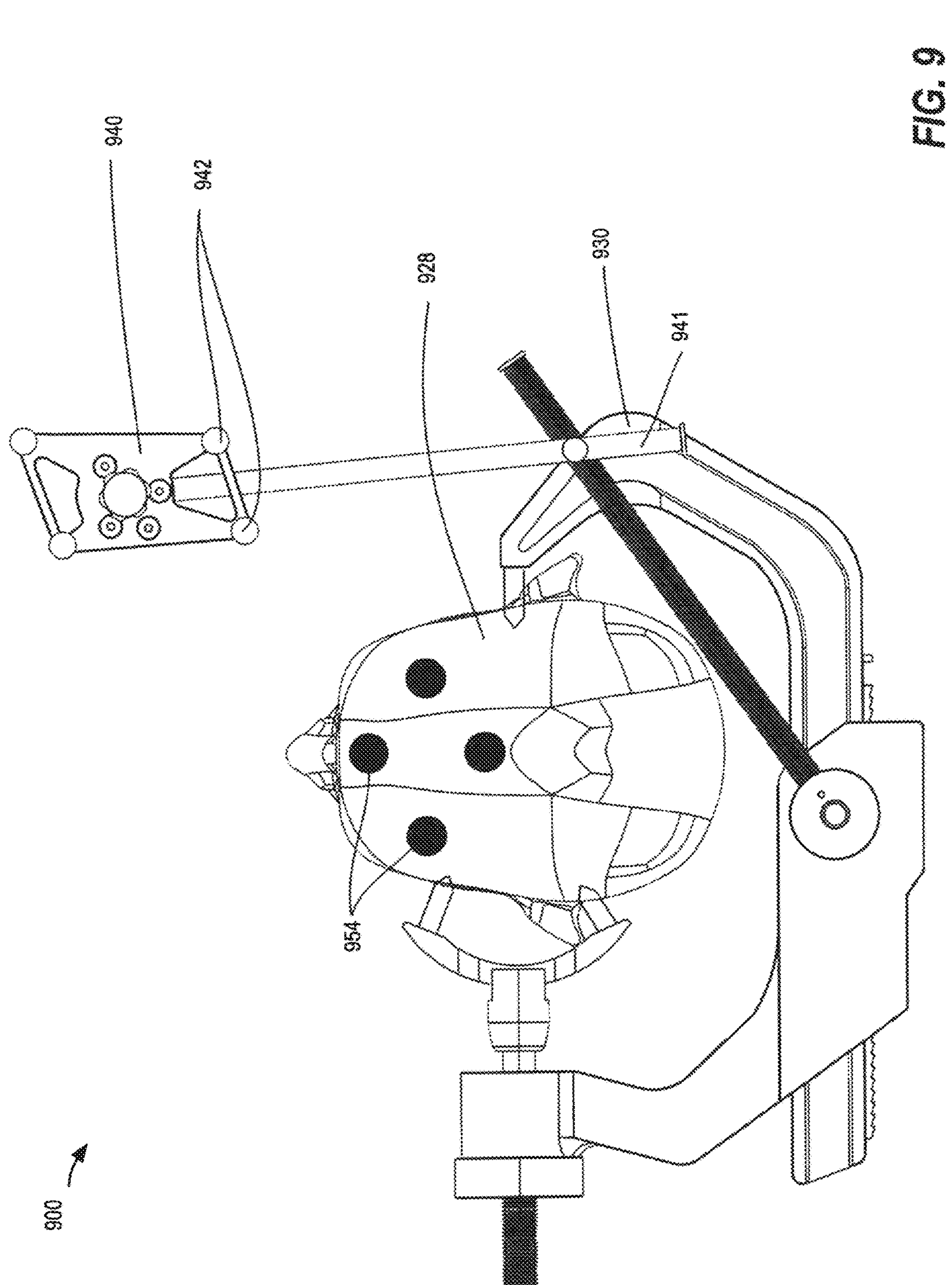
FIG. 9 illustrates a system for registering an anatomical feature of a patient using a navigated probe and fiducials for point-to-point mapping of the anatomical feature, according to some embodiments.

FIG. 9 illustrates a system 900 for registering an anatomical feature of a patient using a navigated or tracked probe and fiducials for point-to-point mapping of the anatomical feature 928 (e.g., a patient's head), according to some embodiments. Software would instruct the user to point with a tracked probe to a series of anatomical landmark points that can be found in the CT or MR image. When the user points to the landmark indicated by software, the system captures a frame of tracking data with the tracked locations of tracking markers on the probe and on the DRB. From the tracked locations of markers on the probe, the coordinates of the tip of the probe are calculated and related to the locations of markers on the DRB. Once 3 or more points are found in both spaces, tracking-to-image registration is achieved. As an alternative to pointing to natural anatomical landmarks, fiducials 954 (i.e., fiducial markers), such as sticker fiducials or metal fiducials, may be used. The surgeon will attach the fiducials 954 to the patient, which are constructed of material that is opaque on imaging, for example containing metal if used with CT or Vitamin E if used with MR. Imaging (CT or MR) will occur after placing the fiducials 954. The surgeon or user will then manually find the coordinates of the fiducials in the image volume, or the software will find them automatically with image processing. After attaching a DRB 940 with tracking markers 942 to the patient through a mounting arm 941 connected to a clamping apparatus 930 or other rigid means, the surgeon or user may also locate the fiducials 954 in physical space relative to the DRB 940 by touching the fiducials 954 with a tracked probe while simultaneously recording tracking markers on the probe (not shown) and on the DRB 940. Registration is achieved because the coordinates of the same points are known in the image space and the tracking space.

One use for the embodiments described herein is to plan trajectories and to control a robot to move into a desired trajectory, after which the surgeon will place implants such as electrodes through a guide tube held by the robot. Additional functionalities include exporting coordinates used with existing stereotactic frames, such as a Leksell frame, which uses five coordinates: X, Y, Z, Ring Angle and Arc Angle. These five coordinates are established using the target and trajectory identified in the planning stage relative to the image space and knowing the position and orientation of the ring and arc relative to the stereotactic frame base or other registration fixture.

Figure 10:
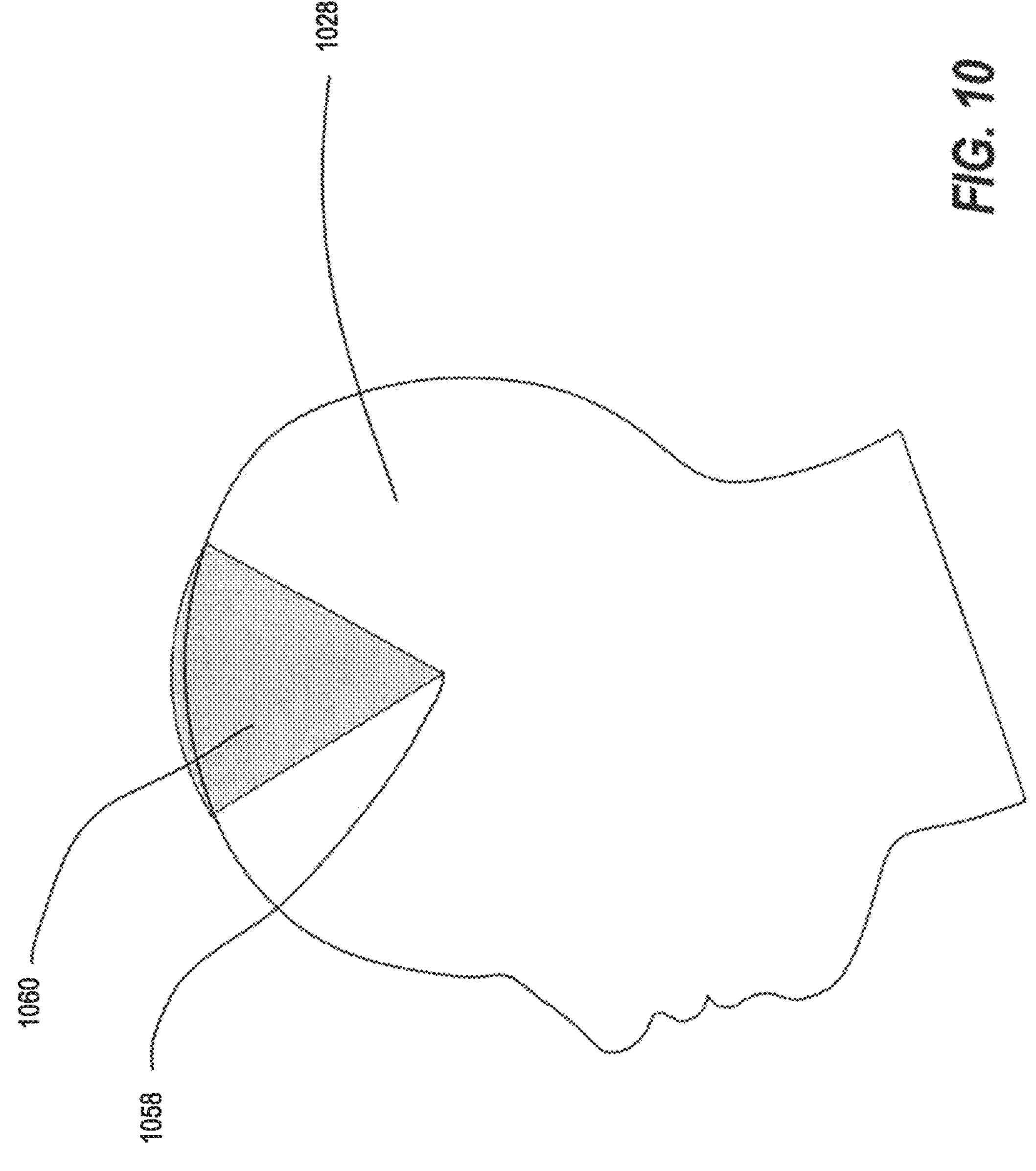
FIG. 10 illustrates a two-dimensional visualization of an adjustment range for a centerpoint-arc mechanism, according to some embodiments.

As shown in FIG. 10, stereotactic frames allow a target location 1058 of an anatomical feature 1028 (e.g., a patient's head) to be treated as the center of a sphere and the trajectory can pivot about the target location 1058. The trajectory to the target location 1058 is adjusted by the ring and arc angles of the stereotactic frame (e.g., a Leksell frame). These coordinates may be set manually, and the stereotactic frame may be used as a backup or as a redundant system in case the robot fails or cannot be tracked or registered successfully. The linear x,y,z offsets to the center point (i.e., target location 1058) are adjusted via the mechanisms of the frame. A cone 1060 is centered around the target location 1058, and shows the adjustment zone that can be achieved by modifying the ring and arc angles of the Leksell or other type of frame. This figure illustrates that a stereotactic frame with ring and arc adjustments is well suited for reaching a fixed target location from a range of angles while changing the entry point into the skull.

Figure 11:
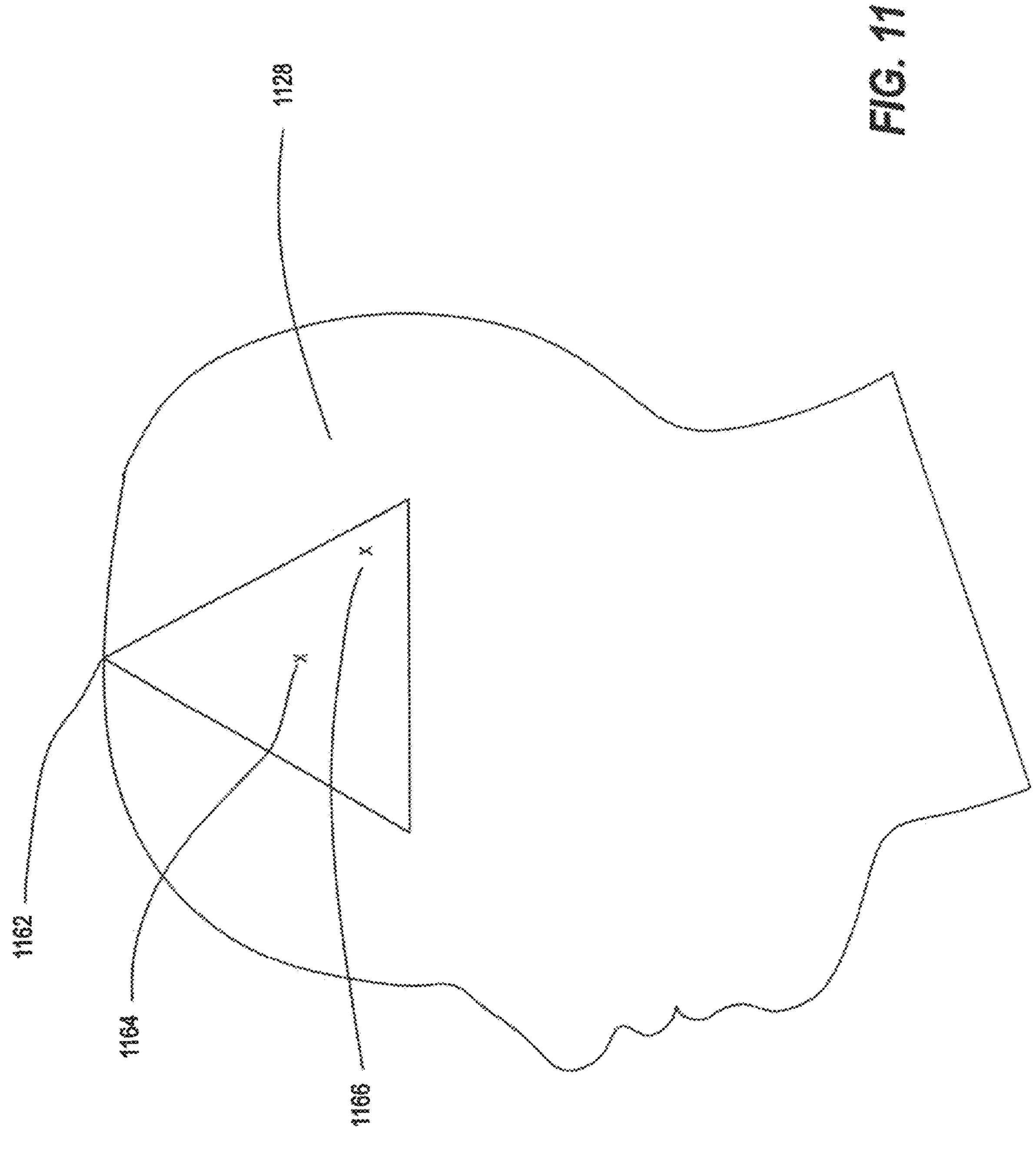
FIG. 11 illustrates a two-dimensional visualization of virtual point rotation mechanism, according to some embodiments.

FIG. 11 illustrates a two-dimensional visualization of virtual point rotation mechanism, according to some embodiments. In this embodiment, the robotic arm is able to create a different type of point-rotation functionality that enables a new movement mode that is not easily achievable with a 5-axis mechanical frame, but that may be achieved using the embodiments described herein. Through coordinated control of the robot's axes using the registration techniques described herein, this mode allows the user to pivot the robot's guide tube about any fixed point in space. For example, the robot may pivot about the entry point 1162 into the anatomical feature 1128 (e.g., a patient's head). This entry point pivoting is advantageous as it allows the user to make a smaller burr hole without limiting their ability to adjust the target location 1164 intraoperatively. The cone 1160 represents the range of trajectories that may be reachable through a single entry hole. Additionally, entry point pivoting is advantageous as it allows the user to reach two different target locations 1164 and 1166 through the same small entry burr hole. Alternately, the robot may pivot about a target point (e.g., location 1058 shown in FIG. 10) within the skull to reach the target location from different angles or trajectories, as illustrated in FIG. 10. Such interior pivoting robotically has the same advantages as a stereotactic frame as it allows the user to approach the same target location 1058 from multiple approaches, such as when irradiating a tumor or when adjusting a path so that critical structures such as blood vessels or nerves will not be crossed when reaching targets beyond them. Unlike a stereotactic frame, which relies on fixed ring and arc articulations to keep a target/pivot point fixed, the robot adjusts the pivot point through controlled activation of axes and the robot can therefore dynamically adjust its pivot point and switch as needed between the modes illustrated in FIGS. 10 and 11.

Following the insertion of implants or instrumentation using the robot or ring and arc fixture, these and other embodiments may allow for implant locations to be verified using intraoperative imaging. Placement accuracy of the instrument or implant relative to the planned trajectory can be qualitatively and/or quantitatively shown to the user. One option for comparing planned to placed position is to merge a postoperative verification CT image to any of the preoperative images. Once pre- and post-operative images are merged and plan is shown overlaid, the shadow of the implant on postop CT can be compared to the plan to assess accuracy of placement. Detection of the shadow artifact on post-op CT can be performed automatically through image processing and the offset displayed numerically in terms of millimeters offset at the tip and entry and angular offset along the path. This option does not require any fiducials to be present in the verification image since image-to-image registration is performed based on bony anatomical contours.

A second option for comparing planned position to the final placement would utilize intraoperative fluoro with or without an attached fluoro fixture. Two out-of-plane fluoro images will be taken and these fluoro images will be matched to DRRs generated from pre-operative CT or MR as described above for registration. Unlike some of the registration methods described above, however, it may be less important for the fluoro images to be tracked because the key information is where the electrode is located relative to the anatomy in the fluoro image. The linear or slightly curved shadow of the electrode would be found on a fluoro image, and once the DRR corresponding to that fluoro shot is found, this shadow can be replicated in the CT image volume as a plane or sheet that is oriented in and out of the ray direction of the fluoro image and DRR. That is, the system may not know how deep in or out of the fluoro image plane the electrode lies on a given shot, but can calculate the plane or sheet of possible locations and represent this plane or sheet on the 3D volume. In a second fluoro view, a different plane or sheet can be determined and overlaid on the 3D image. Where these two planes or sheets intersect on the 3D image is the detected path of the electrode. The system can represent this detected path as a graphic on the 3D image volume and allow the user to reslice the image volume to display this path and the planned path from whatever perspective is desired, also allowing automatic or manual calculation of the deviation from planned to placed position of the electrode. Tracking the fluoro fixture is unnecessary but may be done to help de-warp the fluoro images and calculate the location of the x-ray emitter to improve accuracy of DRR calculation, the rate of convergence when iterating to find matching DRR and fluoro shots, and placement of sheets/planes representing the electrode on the 3D scan.

In this and other examples, it is desirable to maintain navigation integrity, i.e., to ensure that the registration and tracking remain accurate throughout the procedure. Two primary methods to establish and maintain navigation integrity include: tracking the position of a surveillance marker relative to the markers on the DRB, and checking landmarks within the images. In the first method, should this position change due to, for example, the DRB being bumped, then the system may alert the user of a possible loss of navigation integrity. In the second method, if a landmark check shows that the anatomy represented in the displayed slices on screen does not match the anatomy at which the tip of the probe points, then the surgeon will also become aware that there is a loss of navigation integrity. In either method, if using the registration method of CT localizer and frame reference array (FRA), the surgeon has the option to re-attach the FRA, which mounts in only one possible way to the frame base, and to restore tracking-to-image registration based on the FRA tracking markers and the stored fiducials from the CT localizer 536. This registration can then be transferred or related to tracking markers on a repositioned DRB. Once registration is transferred the FRA can be removed if desired.

Figure 12:
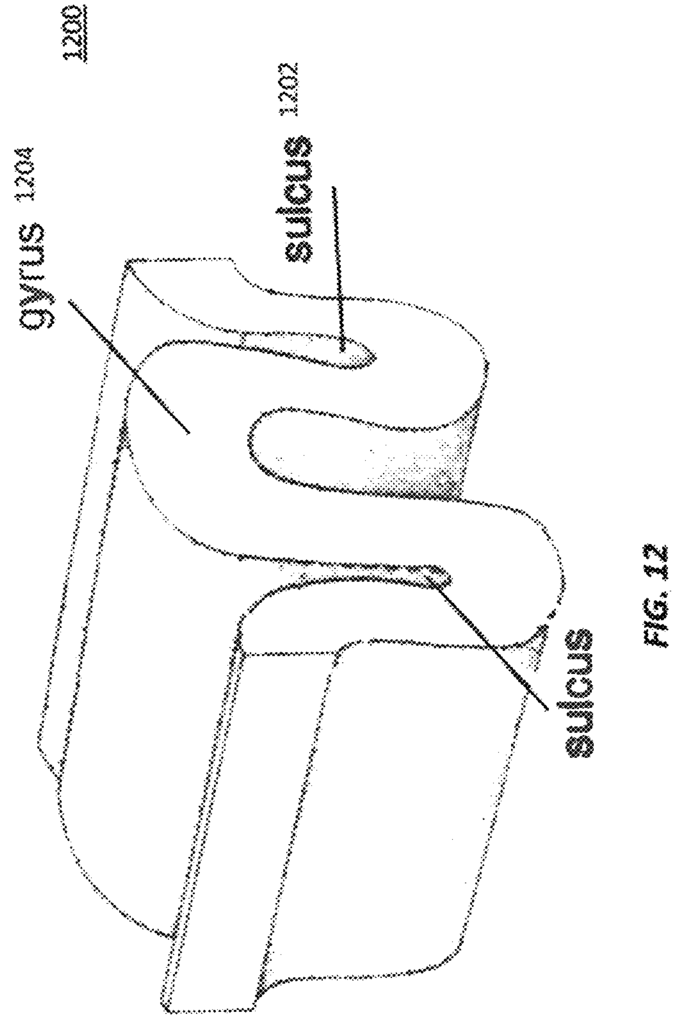

In another embodiment, there is provided a system and method for more efficient placement of electrodes into the brain using the robotic system disclosed above. As background, the brain includes the cerebral cortex 1200 which is comprised of sulci 1202 and gyri 1204, as illustrated in FIG. 12. In an embodiment in which electrodes are positioned within the brain to cause stimulation, the above disclosed robotic system provides a more accurate and efficient system and method for deep brain stimulation (DBS). In an exemplary method, DBS electrodes are positioned in the brain through the gyrus 1204 and avoid penetrating through the sulcus 1202, especially at or near the surface of the cerebral cortex. Similarly, the surgeon avoids passing the electrode through any region of the brain posterior to the coronal bony structure.

Figure 13A:
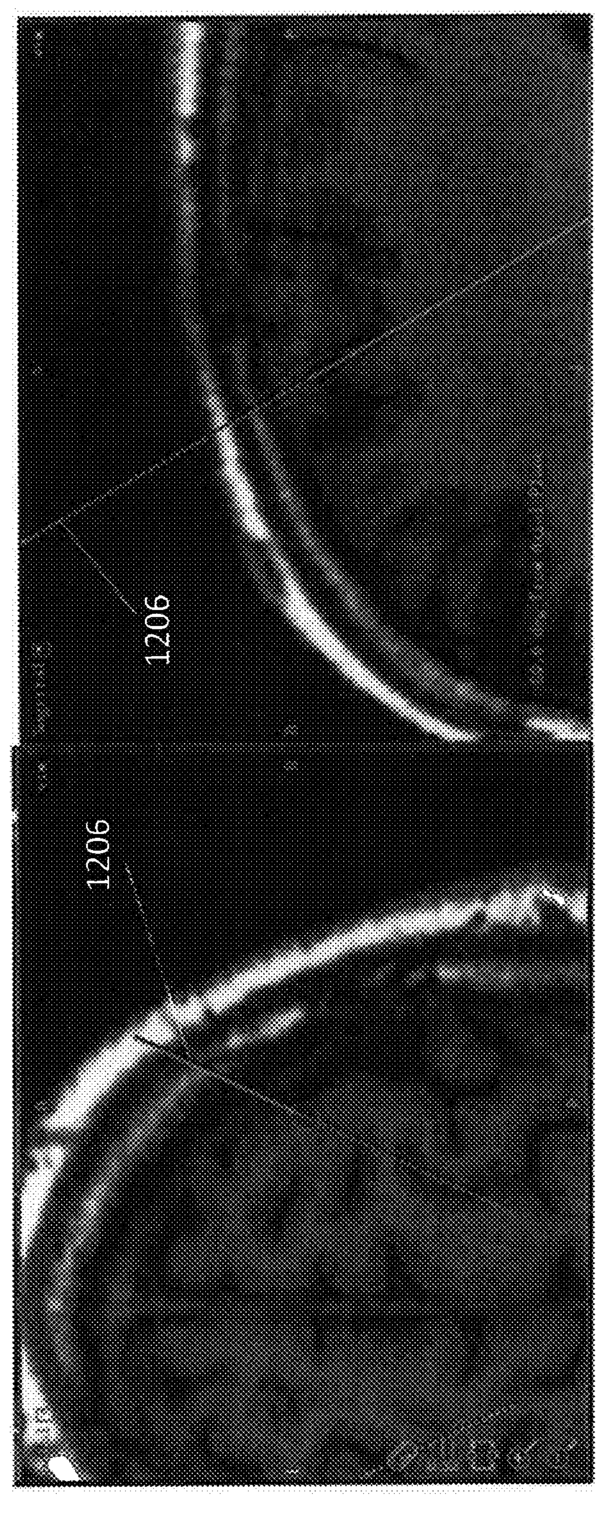
Figure 13B:
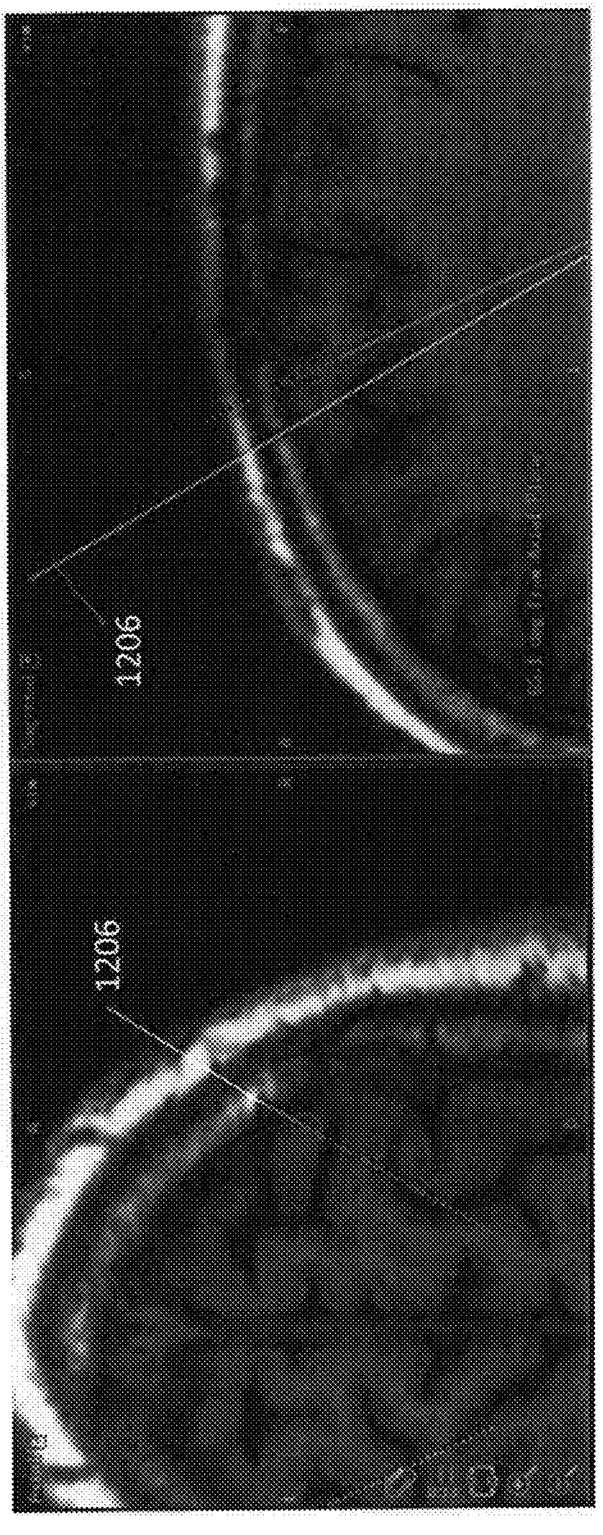

Now turning to FIGS. 13A and 13B, a computer system with software may be used to plan a linear trajectory 206 of an electrode into a target location deep within the brain. The surgeon first selects the target structure (e.g., subthalamic nucleus, globus pallidus interna, ventral intermediate nucleus) and then either estimates a first trajectory based on default angles away from the target, e.g., 15 degrees from the midsagittal plane and 60 degrees from the axial plane (FIG. 13), or requires the user to select an entry point anatomically. By scrolling through an image on the display of the computer system, the surgeon visually evaluates this linear trajectory and manipulates the planned entry position of the electrode into the skull (tail of the electrode) to make adjustments to the plan to try to reduce the frequency of intersection of the electrode path with deep sulci and place the electrode centered through a superficial gyrus. The process of selecting the linear trajectory 1206 can vary depending on which planes the surgeon scrolls on the image when adjusting the trajectory. In other embodiments, the surgeon may adjust the path to the target by avoiding passing through regions of the brain that are known to be responsible for certain cognitive functions, avoiding passing through blood vessels, and avoiding the caudate nucleus.

FIGS. 13A and 13B illustrates the planning a trajectory for positioning an electrode 1206 deep within the brain. Specifically, FIGS. 13A and 13B show planning trajectories on a magnetic resonance image (MRI) of DBS electrodes into the brain. FIG. 13A illustrates the initial plan auto-generated by the software and FIG. 13B illustrates the improved trajectory after manual adjustment by the surgeon.

In an exemplary embodiment of the invention, image processing is used to analyze regions of the brain at and near the first trajectory, predicting and suggesting which direction and by how much the surgeon should move to meet the conditions for optimal placement of the electrode.

For evaluating possible electrode trajectories, image processing enables a small region surrounding the planned path of the electrode to be evaluated to determine the number of times the trajectory passes "in-out-in" through brain folds. To automatically determine whether a feature of the brain is a sulcus or a gyrus, machine learning or template matching may be used, with computerized models trained on the appearance on medical images of a sulcus or gyrus. Alternatively, an image processing algorithm utilized to determine the curvature of an encountered cerebral cortex fold relative to the visceral or parietal direction to determine if the structure is considered a gyrus (convex) or sulcus (concave).

As a result, an accuracy score may be used to determine the best trajectory for placement of the electrode. The accuracy score may be constructed by applying weighting factors to the different considerations according to importance. In another embodiment, if the most important consideration is not penetrating a superficial sulcus, then each penetration of a sulcus would reduce the accuracy score by a greater amount than a less important factor such as distance anterior to the coronal suture. In some embodiments it is more important to avoid superficial sulci than deep sulci, as a result in these embodiments the depth of the encountered sulcus could inversely scale the amount by which the score is reduced. The score would also drop proportionally to the amount by which it is off-center when passing the electrode through a gyrus (i.e., the closer it gets to a sulcus).

In yet another embodiment, the system may provide options for revised and improved trajectories, with the ability to narrow the list of options according to a set of rules provided by the user. In yet another embodiment, the user may visualize options that are within a 10-degree radius of the current location in all directions. The user may also see options that are within a 15-degree radius in a specified plane, such as the coronal plane. In another embodiment, the user may visualize options that increase the accuracy score by greater than 20%.

In another embodiment, the system provides a method for displaying the location or locations of best entry into the skull for the desired target, by generating a map of the surface of the skull or brain that indicates by use of visual characteristics such as colors to indicate the accuracy score of the electrode path according to the criteria determined by the user. In one exemplary embodiment the trajectories of higher accuracy scores could be displayed a color more toward the green end of a red-yellow-green scale and the trajectories of a lower accuracy score may be displayed as a color more toward the red end of the same scale.

In another embodiment, the robot system may be used in an active mode when a surgeon manually drives the robot arm through a range of positions, each representing a different entry point but the same distal target point within the brain. At each position, a computerized meter or a light could indicate to the user the quality of the linear trajectory to the target point. For example, a light mounted on the end effector could glow green when the end effector is moved into a more accurate trajectory, with the light glowing red when moved to a less accurate position. In another embodiment, a gradation of green through yellow through red light may be emitted at different accuracy positions, providing a continuous scale of poor to accurate as the user moves the end effector. In another embodiment, a laser light of varying color and/or intensity may be emitted on the surface of the cranium as the user moves the end effector. Alternately, the system may also utilize haptic feedback to help guide the user to position the end effector accurately. In another embodiment, the surgeon may move the robot arm through a range of possible orientations, each of which has the same target location but different skull entry locations. In yet another embodiment, the robot's end effector is configured to vibrate depending on accuracy score. In other embodiments, various types of vibrations may indicate different degrees of accuracy. In one embodiment, timed vibrations may indicate a more accurate position as the end effector is and no vibrations could indicate an inaccurate positioning. Alternately, the robot system may utilize a "gravity" mode, wherein, when an applied force is applied by the user, the robot arm would automatically position the end effector toward the nearest and most accurate entry location. In another embodiment, an applied force by the user may also move the robot arm off that trajectory and automatically cause the robot arm to move the end effector toward then next closest accurate location with the accuracy score exceeding a base threshold.

Using the methods disclosed above, the present disclosure provides a system and method for the placement of stereo-electroencephalography (Stereo-EEG) depth electrodes. For Stereo-EEG electrodes, a three-dimensional grid of electrodes is placed in targeted brain areas to monitor brain activity and precisely locate seizure sources. In these cases, 2-30 electrodes may be placed within the brain for seizure monitoring. In one embodiment, each individual electrode is positioned at a specific target point. In another embodiment, multiple electrodes may be positioned in specific boundary shape around a target point within the brain. In another embodiment, electrodes may be positioned based on a mean geometric location of an intended 3D grid of target points deep within the brain. The robotic system may then guide the surgeon to an entry location on the skull that allows for an accurate pathway for placing the multiple or grid of electrodes such that the electrodes are spaced apart from the entry point to be above to cover a maximum area. In another embodiment, the robotic system may guide the surgeon to multiple entry points on the brain surface such that for each deep point, the trajectory of the highest accuracy score is utilized. As with the system and methods described above, the system guides the user to one or more options, providing lighting, mapping, or haptic feedback to allow new accurate trajectories that are dynamically selected at the time of surgery.

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Although several embodiments of inventive concepts have been disclosed in the foregoing specification, it is understood that many modifications and other embodiments of inventive concepts will come to mind to which inventive concepts pertain, having the benefit of teachings presented in the foregoing description and associated drawings. It is thus understood that inventive concepts are not limited to the specific embodiments disclosed hereinabove, and that many modifications and other embodiments are intended to be included within the scope of the appended claims. It is further envisioned that features from one embodiment may be combined or used with the features from a different embodiment(s) described herein. Moreover, although specific terms are employed herein, as well as in the claims which follow, they are used only in a generic and descriptive sense, and not for the purposes of limiting the described inventive concepts, nor the claims which follow. The entire disclosure of each patent and patent publication cited herein is incorporated by reference herein in its entirety, as if each such patent or publication were individually incorporated by reference herein. Various features and/or potential advantages of inventive concepts are set forth in the following claims.

What is claimed is:

1. A method for performing a surgical procedure, said method comprising:

providing a system including:

a computer system, a registration fixture, in electronic communication with the computer system, configured to be fixed with respect to an anatomical feature of a patient, a plurality of fiducial markers configured to be fixed with respect to the registration fixture, a tracking data frame defining a tracking space, the tracking data frame including a first plurality of tracked markers that are fixed with respect to the registration fixture, and an electrode;

positioning the electrode within the anatomical feature; and determining, by the computer system, a number of times a planned trajectory of the electrode passes through brain folds.

2. The method of claim 1, wherein the tracking data frame further includes a second plurality of tracked markers that are fixed with respect to a patient support structure, wherein the anatomical feature of the patient is configured to be fixed with respect to the patient support structure, and wherein the computer system is configured to determine, based on the tracking data frame and the determined position of the anatomical feature with respect to the first plurality of tracked markers in the tracking space, a position of the anatomical feature with respect to the second plurality of tracked markers in the tracking space.

3. The method of claim 1, wherein the electrode is positioned in the cerebral cortex based on accuracy score based on a formula determining whether a cerebral cortex structure is a gyrus or a sulcus.

4. The method of claim 3, wherein the electrode positioning is based on a computer generated trajectory that positions the electrode through the gyrus and avoids penetrating the sulcus.

5. The method of claim 3, wherein the accuracy score is determined by the avoidance of the sulcus and distance between the sulcus and an optimal trajectory through the gyrus.

6. The method of claim 1, wherein the system includes a robotic arm coupled to a base.

7. The method of claim 3, wherein a computer generated image of the cerebral cortex is presented and configured to display the locations of multiple trajectories based on the accuracy score.

8. The method of claim 7, wherein the robotic arm is configured to be in an active mode, wherein a user manually moves the robotic arm through a range of positions representing different entry points into the cerebral cortex, wherein an indicator is configured to indicate visually or through haptic feedback the best trajectory based on an accuracy score.

9. The method of claim 8, wherein the haptic feedback is a vibration.

10. A method for performing a medical procedure, said method comprising:

providing a system including:

a computer, a registration fixture, in electronic communication with the computer, configured to be fixed with respect to an anatomical feature of a patient, a plurality of fiducial markers configured to be fixed with respect to the registration fixture, a tracking data frame defining a tracking space, the tracking data frame including a first plurality of tracked markers that are fixed with respect to the registration fixture, and a plurality of Stereo-EEG depth electrodes;

positioning the plurality of Stereo-EEG depth electrodes within the anatomical feature; and determining, by the computer system, a number of times a planned trajectory of one of the plurality of Stereo-EEG depth electrodes passes through brain folds.

11. The method of claim 10, wherein the stereo-EEG depth electrodes are positioned in a three dimensional grid within a cerebral cortex based on an accuracy score determined by a formula generated by whether a portion of the cerebral cortex is a gyrus or a sulcus, and whether access to a target site requires penetration of the sulcus.

12. The method of claim 11, wherein electrode placement of one of the plurality of electrodes is based on a computer generated trajectory that positions the one of the plurality of electrodes through the gyrus and avoids penetrating the sulcus.

13. The method of claim 11, wherein the accuracy score is determined by a avoidance of the sulcus.

14. The method of claim 11, further comprising providing a robotic arm coupled to a base.

15. The method of claim 14, wherein the robotic arm is configured to be in an active mode, wherein a user manually moves the robotic arm through a range of positions representing different entry points into the cerebral cortex, wherein an indicator is configured to indicate visually or through haptic feedback the best trajectory based on the accuracy score.

16. The method of claim 15, wherein the haptic feedback is a vibration.

17. A method for performing a surgical procedure, said method comprising:

providing a robotic system including:

a computer system, a robotic arm coupled to a base, the robotic arm in electronic communication with the computer system, a registration fixture, in electronic communication with the computer system, configured to be fixed with respect to an anatomical feature of a patient, a plurality of fiducial markers configured to be fixed with respect to the registration fixture, a tracking data frame defining a tracking space, the tracking data frame including a first plurality of tracked markers that are fixed with respect to the registration fixture, and an electrode, positioning the electrode within the anatomical feature; and determining, by the computer system, a number of times a planned trajectory of the electrode passes through brain folds.

18. The method of claim 17, wherein the robotic arm is coupled to an end effector.

19. The method of claim 18, wherein the end effector includes a second plurality of tracked markers of the tracking data frame.

20. The method of claim 19, wherein the robotic arm is configured to be in an active mode, wherein a user manually moves the robotic arm through a range of positions representing different entry points into the cerebral cortex, wherein an indicator is configured to indicate visually or through haptic feedback the best trajectory based on an accuracy score.

* * * * *